United States Patent
Rabb et al.

(10) Patent No.: US 10,984,496 B1
(45) Date of Patent: Apr. 20, 2021

(54) THREAT ASSESSMENT AND RESPONSE FACILITATION SYSTEM AND METHOD

(71) Applicant: Credas Inc., Chicago, IL (US)

(72) Inventors: Lionel Rabb, Chicago, IL (US); Jeffrey Morris, Chicago, IL (US); J. Kevin Cameron, Lethbridge (CA); Juan Aramburu, Chicago, IL (US); Michael Rabb, Tampa, FL (US)

(73) Assignee: Credas Inc., Chicago, IL (US)

( * ) Notice: Subject to any disclaimer, the term of this patent is extended or adjusted under 35 U.S.C. 154(b) by 0 days.

(21) Appl. No.: 16/995,964

(22) Filed: Aug. 18, 2020

Related U.S. Application Data

(60) Provisional application No. 62/962,236, filed on Jan. 17, 2020.

(51) Int. Cl.
| | |
|---|---|
| *G06Q 10/10* | (2012.01) |
| *G06Q 10/08* | (2012.01) |
| *G06Q 30/02* | (2012.01) |
| *G06Q 40/08* | (2012.01) |
| *G06Q 50/26* | (2012.01) |
| *G06F 21/60* | (2013.01) |
| *G06F 21/62* | (2013.01) |
| *G06F 9/54* | (2006.01) |
| *G06Q 50/00* | (2012.01) |
| *G06N 5/04* | (2006.01) |
| *H04L 29/08* | (2006.01) |
| *G09B 19/00* | (2006.01) |
| *G06N 20/00* | (2019.01) |

(52) U.S. Cl.
CPC ............ *G06Q 50/265* (2013.01); *G06F 9/54* (2013.01); *G06F 21/604* (2013.01); *G06F 21/62* (2013.01); *G06N 5/04* (2013.01); *G06N 20/00* (2019.01); *G06Q 50/01* (2013.01); *G09B 19/00* (2013.01); *H04L 67/20* (2013.01); *H04L 67/22* (2013.01); *G06Q 10/1093* (2013.01)

(58) Field of Classification Search
CPC .. G06Q 50/265; G06Q 50/01; G06Q 10/1093; G06F 21/604; G06F 21/62; G06F 9/54; G06N 5/04; G06N 20/00; G09B 19/00; H04L 67/20; H04L 67/22
USPC .................................. 705/1.1–912, 319, 325
See application file for complete search history.

(56) References Cited

U.S. PATENT DOCUMENTS

| | | | |
|---|---|---|---|
| 7,343,302 B2 * | 3/2008 | Aratow | G06Q 50/265 705/325 |
| 7,346,492 B2 * | 3/2008 | Shaw | G06F 21/316 704/9 |

(Continued)

*Primary Examiner* — Jonathan P Ouellette
(74) *Attorney, Agent, or Firm* — Nyman IP LLC; Scott Nyman

(57) ABSTRACT

A threat assessment and response facilitation system is provided for facilitating communication relating to threat assessment, responding to a traumatic event, and provision of training materials for professionals engaged in threat assessment and trauma response activities. The threat assessment and trauma response facilitation system may include modules such as a threat assessment assistance module, learning portal module, client portal module, response coordination module, training broker module, and messaging module. A method for facilitating communication relating to threat assessment and trauma response using the threat assessment and response facilitation system is also provided.

19 Claims, 14 Drawing Sheets

(56) References Cited

U.S. PATENT DOCUMENTS

| | | | | |
|---|---|---|---|---|
| 8,515,049 | B2* | 8/2013 | Chavez | G06F 16/951 |
| | | | | 379/265.02 |
| 10,043,366 | B2* | 8/2018 | Gorzela | H04L 67/22 |
| 10,074,257 | B2* | 9/2018 | Wang | G08B 21/02 |
| 2002/0143469 | A1* | 10/2002 | Alexander | A62B 99/00 |
| | | | | 702/2 |
| 2005/0182722 | A1* | 8/2005 | Meyer | G06Q 10/06 |
| | | | | 705/40 |
| 2008/0172352 | A1* | 7/2008 | Friedlander | G06N 7/08 |
| | | | | 706/46 |
| 2008/0175266 | A1* | 7/2008 | Alperovitch | G06Q 10/107 |
| | | | | 370/465 |
| 2012/0197896 | A1* | 8/2012 | Li | G06F 16/313 |
| | | | | 707/740 |
| 2014/0368601 | A1* | 12/2014 | deCharms | H04L 65/403 |
| | | | | 348/14.02 |
| 2015/0161867 | A1* | 6/2015 | Bell | G08B 21/22 |
| | | | | 340/539.13 |
| 2015/0163312 | A1* | 6/2015 | Maguire | G16H 50/80 |
| | | | | 709/219 |
| 2015/0370993 | A1* | 12/2015 | Moturu | G16H 50/50 |
| | | | | 703/6 |
| 2016/0330601 | A1* | 11/2016 | Srivastava | B64C 39/024 |
| 2017/0148241 | A1* | 5/2017 | Kerning | G08B 27/006 |
| 2017/0236229 | A1* | 8/2017 | Roof | G06K 9/00577 |
| | | | | 705/345 |
| 2017/0346776 | A1* | 11/2017 | Valla | H04L 51/28 |
| 2017/0374093 | A1* | 12/2017 | Dhar | H04L 63/1433 |
| 2019/0130719 | A1* | 5/2019 | D'Amico | G06F 9/44 |
| 2019/0304042 | A1* | 10/2019 | Santell | G06Q 50/01 |

* cited by examiner

THREAT ASSESSMENT AND RESPONSE FACILITATION SYSTEM AND METHOD

CROSS-REFERENCE TO RELATED APPLICATION

This application claims the priority from U.S. provisional patent application Ser. No. 62/962,236 filed Jan. 17, 2020. The foregoing application is incorporated in its entirety herein by reference.

FIELD OF THE INVENTION

The present disclosure relates to a threat assessment and response facilitation system. More particularly, the disclosure relates to facilitating communication, assessing threats and risk of violence and divergent behavior, and facilitating response to a traumatic event.

BACKGROUND

Traumatic events are extremely unfortunate and can cost society in many ways, most notably the loss of some of its members lives. Examples of traumatic events include school shootings, violent rallies, terrorist attacks, extremist events, pandemics, outbreaks, illness, or other actions that threaten or harm the lives or safety of others.

While society as a whole may never be able to completely eliminate traumatic events, as divergent personalities and individuals may not act consistently with the goals of the society at large, goals must be set to improve the detection of a risk indicative of a violent behavior or possible traumatic event. Research is constantly being performed on what may cause a person to engage in violent or traumatic behavior, including what may trigger such a behavior and how such a reaction may be avoided. However, coordination of academics, response, and actions of other individuals involved in mitigating the risk of a traumatic event in management of a situation should such an event occur requires great improvement to help combat this threat to our society.

Very few resources appear to be available for assisting schools, businesses, health care facilities, and related professionals with understanding the impact of trauma on systems and how to respond in ways that allow schools and communities to deal with the tragedies in a way that fosters growth rather than divisiveness and encourages healing rather than long-term symptom development. No known tools treat the growing concern regarding student threats and the aftermath of a traumatic event, considers the effect of experiencing a traumatic event on the mental state of those affected, or coordinates trained professionals and responding parties to be better able to identify risks of future potentially avoidable events.

No known platform, tool, system, or other useful feature exists for professionals involved in mitigating and responding to traumatic events that facilitate learning aspects, training, communication, coordination, selection of the best professionals for a given violent or divergent behavior event or health crisis; collective sharing of information between agencies and responders; and other essential aspects of dealing with such a consequential situation. This disclosure is provided to describe features of a tool designed to combat what appears to be an increasing prevalence of traumatic events, including violent events and threats.

Therefore, a need exists to solve the deficiencies present in the prior art. What is needed is a system to facilitate communication between parties to assist with assessment of risk of a violent threat and related effects to physical and mental health. What is needed is a computerized system to assist with detecting and responding to threats of potential violent behavior and related effects to physical and mental health. What is needed is a computerized system to encourage users to enhance their knowledge in detecting and responding to threats. What is needed is a computerized system including a learning platform to serve educational materials for consumption by users to enhance ability to detect threats and respond to same. What is needed is a method of educating users, detecting threats, and facilitating responses to same using a system operable on a computer. What is needed is a system for, and method of, collecting information relating to a traumatic health crisis, increasing knowledge, and understanding relating to the traumatic health crisis, and assisting with organizing responders to mitigate the effects of a traumatic health crisis. What is needed is a system for, and method of, managing physical and mental health of individuals with regard to risks, threats, and responses to same. What is needed is a system and method for responding to a traumatic event and assisting with coordination of responders to same.

SUMMARY

An aspect of the disclosure advantageously provides a system to facilitate communication between parties to assist with assessment of risk of a violent threat and related effects to physical and mental health. An aspect of the disclosure advantageously provides a computerized system to assist with detecting and responding to threats of potential violent behavior and related effects to physical and mental health. An aspect of the disclosure advantageously provides a computerized system to encourage users to enhance their knowledge in detecting and responding to threats. An aspect of the disclosure advantageously provides a computerized system including a learning platform to serve educational materials for consumption by users to enhance an ability to detect threats and respond to same. An aspect of the disclosure advantageously provides a method of educating users, detecting threats, and facilitating responses to same using a system operable on a computer. An aspect of this disclosure advantageously provides a system for, and method of, collecting information relating to a traumatic health crisis, increasing knowledge and understanding relating to the traumatic health crisis, and assisting with organizing responders to mitigate the effects of a traumatic health crisis. An aspect of the disclosure advantageously provides a system for, and method of, managing physical and mental health of individuals with regard to risks, threats, and responses to same. An aspect of the disclosure advantageously provides a system and method for responding to a traumatic event and assisting with coordination of responders to same.

The threat assessment assistance module and/or other modules includable in a system enabled by this disclosure may advantageously benefit from a novel multiple disciplinary collaboration between multiple users and professionals with differing and/or complimentary perspectives, allowing information to be easily aggregated and analyzed to produce more useful results. Machine learning may be applied to the information received through the threat assessment assistance module to assist with detecting patterns and identifying correlations between stimuli and reactive events. By using modules such as the threat assessment assistance module, multiple disciplinary professionals may decrease the likelihood that managing large sets of information will become overwhelming and resulting diminished utility from the overwhelmed analysis inherent to a disfavored unidimensional approach.

Tools, systems, platforms, and methods are described throughout this disclosure that advantageously assist with detecting indicators that a violent threat, risk of a traumatic event, or developing health crisis are present. The tools provided by the systems and methods described throughout this disclosure additionally allow professionals to pursue meaningful investigation into these indicators and perform the appropriate proactive steps. The systems and methods enabled by this disclosure assist with data collection and immediate risk reducing interventions that advantageously assist with mitigating the general risk of violent behavior that affects large numbers of people or the society at large. By identifying threat assessments in general violence risk assessments, a more comprehensive combination of tools and assessments may be provided to improve intervention, increase the mitigation of undesirable traumatic events, and adequately respond to such an event should one occur.

According to an embodiment of this disclosure, a threat assessment and response facilitation system is provided that can be operated on a computerized device comprising a processor and memory. The system may be operated by execution of electronic instructions stored by and read from the memory. The system may include modules, wherein each module of the modules may include a component, a database, and an application programming interface (API). The component may execute at least part of the electronic instructions. The database may be siloed with the module and may be communicably connected to the component to store the at least part of the electronic instructions and data associated with the module. The API may communicate with a requesting entity having sufficient permissions regarding at least part of the data included by the database associated with the module and to affect operation of the component included by the module.

The data stored by the database may be made directly available to the component of the module. The data stored by the database may be made selectively available to the requesting entity via the API as governed by the permissions. A permissions structure may be controlled by at least one of the modules designated to manage the permissions to selectively grant access to exchange the at least part of the data stored by the database of the module and request execution of the at least part of the electronic instructions of the component of the module. A communication structure may be controlled by at least one of the modules designated to manage communications to selectively transfer the at least part of the data between the module and the requesting entity as permitted by the permissions structure via the API of the module.

The modules may include a threat assessment assistance module, a response coordination module, and a client portal module. Other modules may be included. The threat assessment assistance module may include a profiles and peoples component for identifying a person of concern and organizing the data relating to the person of concern. The threat assessment assistance module may include a worrisome behavior component for monitoring worrisome behavior associated with the person of concern. The threat assessment assistance module may include an analytics component to analyze information relating to the person of concern to maintain a record and recommend activity corresponding with the record. The threat assessment assistance module may include a risk enhancers component for monitoring conditions affecting risk of harm to the person of concern and others.

The response coordination module may include a scheduling component for organizing responders for deployment to a site of a traumatic event. The response coordination module may include a resources component for requesting resources to support the responders. The response coordination module may include an information management component for managing the information sharable among the responders.

The client portal module may include a profiles component for managing the information associated with a user. The client portal module may include a graphical user interface (GUI) displayable to the user. External applications having the permissions that are sufficient may be selectively communicable with at least some of the modules and the data associated with the at least some of the modules for which the access is permitted.

In another aspect, the threat assessment assistance module further may include a genogram component to organize the information relating to familial organization including genealogy and the worrisome behavior associated with a family member of the person of concern. The information provided by the genogram component may be analyzed by the threat assessment assistance module to derive insight relating to the person of concern.

In another aspect, the threat assessment assistance module further may include a social media analysis request component to communicate with a third-party data reporting service that monitors social media network activity of the person of concern. The third-party data reporting service may communicate with the social media analysis request component via the API.

In another aspect, the threat assessment assistance module further may include a domains and beliefs component to assess a change in domain-focused factors and a change in belief-focused factors indicative of a change in behavior of the person of concern.

In another aspect, the threat assessment assistance module further may include a machine learning engine to compare at least part of the data included by the database of the threat assessment assistance module to identify correlations and predict a statistical probability of the worrisome behavior.

In another aspect, the threat assessment assistance module may be communicably connected to an external web application. The external web application may include an outreach component to provide a channel of communication for submission of the information relating to the person of concern by a third party. The information may be includable in the database of the threat assessment assistance module. The external web application may include a self-assessment component to facilitate self-assessment of an emotional condition by the user to be associated with the user.

In another aspect, the modules further include a mobile application module to provide access to the client portal module via a portable electronic device and notifications and alerts relating to the user.

In another aspect, the response coordination module further includes a stipend management component to manage disbursement of stipends and payments relating to the deployment.

In another aspect, the client portal module further includes a gamification component to reward engagement with the system and provide incentives to continue the engagement.

In another aspect, the modules further include a learning portal module. The learning portal module may include educational content stored in the database associated with the learning portal module. The learning portal module may include a certificate and accreditation component to manage qualifications for participating in the deployment and access to the at least part of the data associated with the threat assessment assistance module. The learning portal module may include a participation component to manage enrollment, attendance, and grading relating to the educational content.

In another aspect, the modules may further include a training broker module. The training broker module may include a training seats component to manage an assignment of user rights to participate in events and access the educational content hosted by the learning portal module. The training broker module may include an approvals component to manage the assignment of user rights by a host of the events and the educational content. The training broker module may include an e-commerce component for managing a transfer of funds associated with the assignment of user rights.

In another aspect, the modules further may include a messaging module to provide communication among the users of the modules.

In another aspect, the communication structure may provide a direct communication pathway between the modules that are directly connected via the API. The communication structure may provide a bridged communication pathway between the modules that are indirectly connected via the API by sharing at least one intermediary module being communicably connected to the modules via the API. The intermediary module may relay the communication received by a first connected module via a first API pathway to a second connected module via a second API pathway.

According to an embodiment enabled by this disclosure, a threat assessment and response facilitation system is provided that is operable on a computerized device comprising a processor and memory. The system may be operated by execution of electronic instructions stored by and read from the memory. The system includes modules, wherein each module of the modules includes a component, a database, and an API. The component may execute at least part of the electronic instructions. The database may be communicably connected to the component to store the at least part of the electronic instructions and data associated with the module. The application programming interface (API) may communicate with a requesting entity having sufficient permissions at least part of the data included by the database associated with the module and to affect operation of the component included by the module. Data stored by the database may be directly available to the component of the module. Data stored by the database may be selectively available to the requesting entity via the API as governed by the permissions.

A permissions structure controlled by at least one of the modules designated to manage the permissions may be provided to selectively grant access to exchange the at least part of the data stored by the database of the module and request execution of the at least part of the electronic instructions of the component of the module. A communication structure controlled by at least one of the modules designated to manage communications may be provided to selectively transfer the at least part of the data between the module and the requesting entity as permitted by the permissions structure via the API of the module.

The modules may include a threat assessment assistance module, a response coordination module, a client portal module, and a messaging module.

The threat assessment assistance module may include a profiles and peoples component for identifying a person of concern and organizing the data relating to the person of concern. The threat assessment assistance module may include a worrisome behavior component for monitoring worrisome behavior associated with the person of concern. The threat assessment assistance module may include an analytics component to analyze information relating to the person of concern to maintain a record and recommend activity corresponding with the record. The threat assessment assistance module may include a machine learning engine to compare the at least part of the data included by the database of the threat assessment assistance module to identify correlations and predict a statistical probability of the worrisome behavior.

The response coordination module may include a scheduling component for organizing responders for deployment to a site of a traumatic event. The response coordination module may include a resources component for requesting resources to support the responders. The response coordination module may include an information management component for managing information sharing among the responders.

The client portal module may include a profiles component for managing the information associated with a user. The client portal module may include a gamification component to reward engagement with the system and incentivize continued engagement.

The messaging module may provide communication among the users of the modules.

External applications having the permissions that are sufficient may be selectively communicable with at least some of the modules and the data associated with the at least some of the modules for which the access is permitted. The communication structure may provide a direct communication pathway between the modules that are directly connected via the API. The communication structure may provide a bridged communication pathway between the modules that are indirectly connected via the API by sharing at least one intermediary module being communicably connected to the modules via the API. The intermediary module may relay the communication received by a first connected module via a first API pathway to a second connected module via a second API pathway.

In another aspect, the threat assessment assistance module may further include a genogram component to organize the information relating to familial organization including genealogy and the worrisome behavior associated with a family member of the person of concern. Information provided by the genogram component may be analyzed by the threat assessment assistance module to derive insight relating to the person of concern. A domains and beliefs component may be provided to assess a change in domain-focused factors and a change in belief-focused factors indicative of a change in behavior of the person of concern. A risk enhancers component may be provided for monitoring conditions affecting risk of harm to the person of concern and others.

In another aspect, the threat assessment assistance module may further include a social media analysis request component to communicate with a third-party data reporting service that monitors social media network activity of the person of concern. The third-party data reporting service may communicate with the social media analysis request component via the API. The threat assessment assistance module may be communicably connected to an external web application. The external web application may include an outreach component to provide a channel of communication for submission of the information relating to the person of concern by a third party. The information may be includable in the database of the threat assessment assistance module. The external web application may include a self-assessment component to facilitate self-assessment of an emotional condition by the user to be associated with the user.

In another aspect, the modules may further include a learning portal module. The learning portal module may include educational content stored in the database associated with the learning portal module. The learning portal module may include a certificate and accreditation component to manage qualifications for participating in the deployment and access to the at least part of the data associated with the threat assessment assistance module. The learning portal module may include a participation component to manage enrollment, attendance, and grading relating to the educational content.

In another aspect, a training broker module may be provided, which may include a training seats component, an approvals component, and an e-commerce component. The training seats component may manage an assignment of user rights to participate in events and access the educational content hosted by the learning portal module. The approvals component may manage the assignment of user rights by a host of the events and the educational content. The e-commerce component may manage a transfer of funds associated with the assignment of user rights.

According to an embodiment of this disclosure, a method is provided for assessing a threat and facilitating a response using a threat assessment and response facilitation system operated on a computerized device comprising a processor and memory. The method may be operated by execution of electronic instructions stored by and read from the memory.

The method may include a) operating modules, wherein each module of the modules includes a component, a database, and an API. The component may execute at least part of the electronic instructions. The database may be siloed with the module and may be communicably connected to the component to store the at least part of the electronic instructions and data associated with the module. The API may communicate with a requesting entity having sufficient permissions at least part of the data included by the database associated with the module and to affect operation of the component included by the module. The data stored by the database may be directly available to the component of the module. The data stored by the database may be selectively available to the requesting entity via the API as governed by the permissions.

The method may include b) managing permissions via a permissions structure to selectively grant access to exchange the at least part of the data stored by the database of the module and request execution of the at least part of the electronic instructions of the component of the module. The method may include c) managing communications via a communication structure to selectively transfer the at least part of the data between the module and the requesting entity as permitted by the permissions structure via the API of the module. The method may include d) providing a direct communication pathway between the modules that are directly connected via the API. The method may include e) providing a bridged communication pathway between the modules that are indirectly connected via the API by sharing at least one intermediary module being communicably connected to the modules via the API, wherein the intermediary module relays the communication received by a first connected module via a first API pathway to a second connected module via a second API pathway.

The modules may include at least a threat assessment assistance module, a response coordination module, and a client portal module. The threat assessment assistance module may be operable for i) identifying a person of concern and organizing the data relating to the person of concern via a profiles and peoples component, ii) monitoring worrisome behavior associated with the person of concern via a worrisome behavior component, iii) analyzing information relating to the person of concern to maintain a record and recommend activity corresponding with the record via an analytics component, and iv) monitoring conditions affecting risk of harm to the person of concern and others via a risk enhancers component. The response coordination module may be operable for v) organizing responders for deployment to a site of a traumatic event via a scheduling component, vi) requesting resources to support the responders via a resources component, and vii) managing information sharing among the responders via an information management component. The client portal module may be operable for viii) managing the information associated with a user via a profiles component and ix) displaying a graphical user interface (GUI) to the user.

The method may include f) comparing at least part of the data included by the database of the threat assessment assistance module to identify correlations and predict a statistical probability of the worrisome behavior via a machine learning engine. The method may include g) selectively communicating among external applications having the permissions that are sufficient and at least some of the modules and the data associated with the at least some of the modules for which the access is permitted. The method may include h) providing the communications among the users of the modules via a messaging module.

In another aspect of the method, operating the threat assessment assistance module may include x) organizing the information relating to familial organization including genealogy and the worrisome behavior associated with a family member of the person of concern via a genogram component. Operating the threat assessment assistance module may include xi) analyzing the information provided by the genogram component by the threat assessment assistance module and deriving insight relating to the person of concern from the information. Operating the threat assessment assistance module may include xii) communicating with a third-party data reporting service that monitors social media network activity of the person of concern via a social media analysis request component, wherein the third-party data reporting service communicates with the social media analysis request component via the API. Operating the threat assessment assistance module may include xiii) predicting a change in behavior of the person of concern via a domains and beliefs component by assessing a change in domain-focused factors and a change in belief-focused factors.

In another aspect of the method, the modules may further include a learning portal module for xiv) distributing educational content stored in the database associated with the learning portal module, xv) managing qualifications for participating in the deployment and the access to the at least part of the data associated with the threat assessment assistance module via a certificate and accreditation component, and xvi) managing enrollment, attendance, and grading relating to the educational content via a participation component.

In another aspect, external web applications may include components such as an assist component and an outreach component. The assist component may advantageously facilitate a third party with submitting an incident report or concern to operators of a threat assessment assistance module. The assist component may receive externally provided tips and may operate using a black box environment to at least partially anonymize the source of received information.

The outreach component may advantageously facilitate referral for professionals and other people to interact with the various modules provided by a system and enabled by this disclosure. The outreach component may advantageously provide authenticated user-based sharing of information and other data.

Terms and expressions used throughout this disclosure are to be interpreted broadly. Terms are intended to be understood respective to the definitions provided by this specification. Technical dictionaries and common meanings understood within the applicable art are intended to supplement these definitions. In instances where no suitable definition can be determined from the specification or technical dictionaries, such terms should be understood according to their plain and common meaning. However, any definitions provided by the specification will govern above all other sources.

Various objects, features, aspects, and advantages described by this disclosure will become more apparent from the following detailed description, along with the accompanying drawings in which like numerals represent like components.

DETAILED DESCRIPTION

Figure 1:
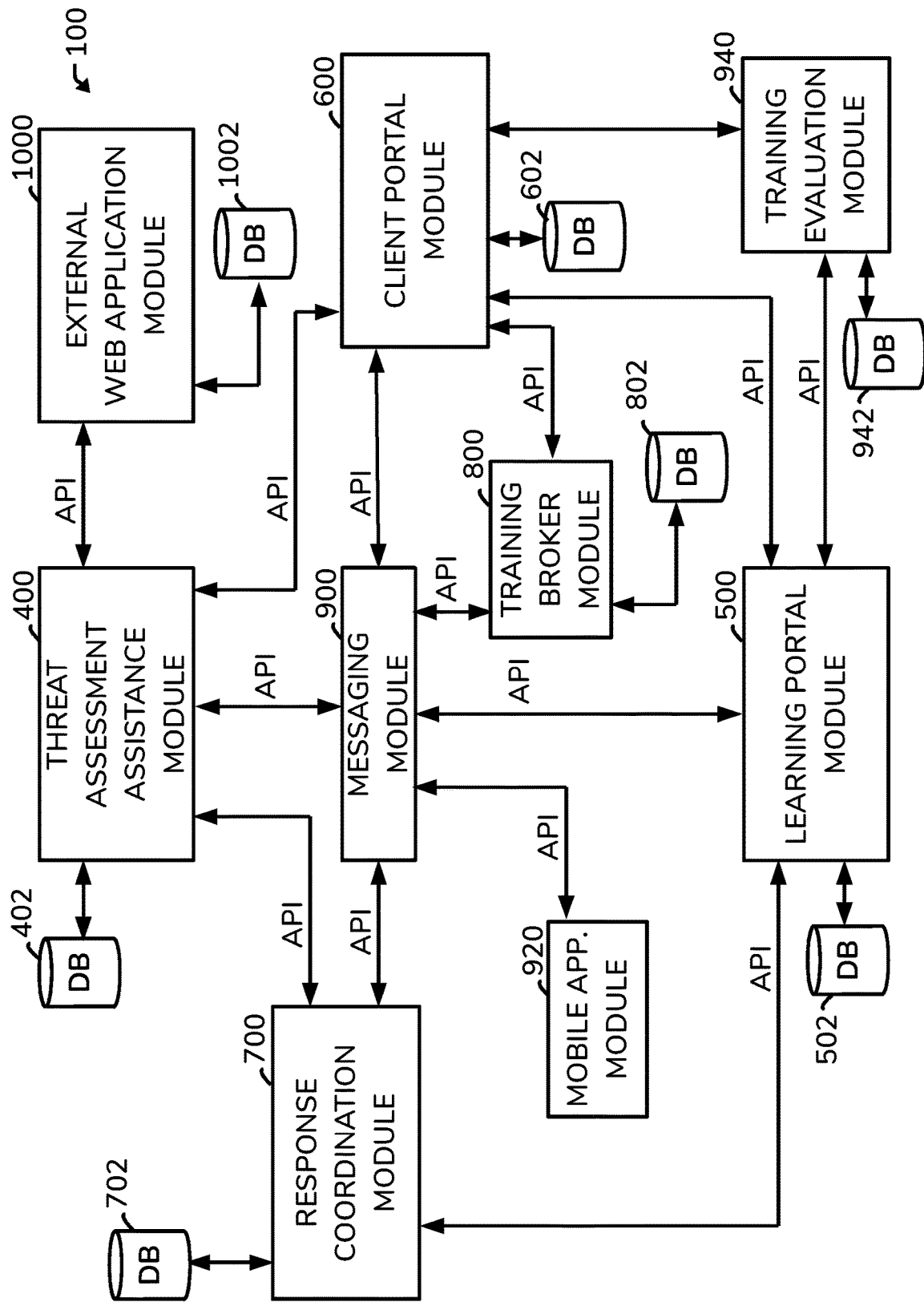
FIG. 1 is a block diagram view of an illustrative threat assessment and communication facilitation tool, according to an embodiment of this disclosure.

The following disclosure is provided to describe various embodiments of a threat assessment and response facilitation system. Skilled artisans will appreciate additional embodiments and uses of the present invention that extend beyond the examples of this disclosure. Terms included by any claim are to be interpreted as defined within this disclosure. Singular forms should be read to contemplate and disclose plural alternatives. Similarly, plural forms should be read to contemplate and disclose singular alternatives. Conjunctions should be read as inclusive except where stated otherwise.

Expressions such as "at least one of A, B, and C" should be read to permit any of A, B, or C singularly or in combination with the remaining elements. Additionally, such groups may include multiple instances of one or more element in that group, which may be included with other elements of the group. All numbers, measurements, and values are given as approximations unless expressly stated otherwise.

For the purpose of clearly describing the components and features discussed throughout this disclosure, some frequently used terms will now be defined, without limitation. The term application programming interface (API), as it is used throughout this disclosure, is defined as a set of functions and procedures allowing sharing of data between different applications and modules of a common application based on permissions. The term custodial data model, as it is used throughout this disclosure, is defined as management of data using permissions and controlled distribution.

The term module, as it is used throughout this disclosure, is defined as a substantially self-contained hardware and/or software component that may interact with a larger system, for example, as a software module operable by executing electronic instructions that typically handles a specific task or set of tasks within a larger software system. The term component, as it is used throughout this disclosure, is defined as a part of a system or application that may break the complexity of a software module or other aspect of the system into manageable operations and parts. The term requesting entity, as it is used throughout this disclosure, is defined as a module, component, or other outside entity requesting to communicate data with another module, component, or other entity. In one example, a requesting entity may be a module requesting communication of data with another module of a system, without limitation. The term silo or siloed database, as it is used throughout this disclosure, is defined as a segregation of data being readily accessible within an associated module, with the data being accessible by requesting entities having sufficient permissions, for example, via an API.

The term threat, as it is used throughout this disclosure, is defined as a possibility of a violent or divergent behavior, for example, diverging from a baseline behavior. The term baseline behavior, as it is used throughout this disclosure, is defined as a typical behavior for an individual and/or group that can serve as a baseline for future reference. The term fluidity, as it is used throughout this disclosure, is defined as an interaction between the suicidal and homicidal domains. The term traumatic event, as it is used throughout this disclosure, is also referred to as a traumatic incident and defined as an event causing traumatic influence on individuals or society, such as a school shooting, mass-violence event, outbreak, health emergency, pandemic, or other incidents that would be apparent to a person of skill in the art after having the benefit of this disclosure.

The term detection, as it is used in this disclosure in the context of threat detection, is intended to include analyzing available information to affect a determination of whether a violent and/or divergent event may occur. The term assessment, as it is used in this disclosure in the context of threat assessment, is intended to include analyzing an identified threat to determine the severity of such threat and to determine a suggested follow up action to same. Those of skill in the art will appreciate that some assessments may include elements of detection and some detections may include an element of assessment, without limitation. The term critical period, as it is used throughout this disclosure, is defined as a predictable time frame for increased threat making or threat-related behavior in the aftermath of individual and/or high profile traumas, that may exist in individuals, families, communities, or larger human systems, for example, an anniversary or other significant date or timeframe in relation to a past traumatic event and/or trigger.

The term person of concern, as it is used throughout this disclosure, is defined as a person having indications of increased risk and/or threat for violent or divergent behavior. The term adverse childhood experiences, as it is used throughout this disclosure, is defined as a potentially traumatic event that occurs in childhood, such as experiencing violence or abuse, witnessing violence in the home or community, exposure to a family member attempting or dying by suicide, substance abuse, mental health problems, incarceration of a family member, and other traumatic events.

The term threat assessment, as it is used throughout this disclosure, is defined as the process of determining if a threat maker actually poses a risk to the target or targets they have threatened. The term risk assessment, as it is used throughout this disclosure, is defined as the process of determining if an individual and/or group may pose a future risk to a known or unknown target or targets in an unknown period of time, wherein a risk may not require a known threat to have been made. For the purpose of this and related examples, a group is intended to include more than one individual. The term worrisome behavior, as it is used throughout this disclosure, is defined as behaviors that cause concern for members of an organization, workplace, school, or community system that may indicate that an individual and/or group is moving toward a risk of serious violent and/or divergent behavior.

The term gamification, as it is used throughout this disclosure, is defined as inclusion of scoring, point accumulation, or other actual and/or virtual incentives to engage with a platform and/or service. The term badge, as it is used throughout this disclosure, is defined as an accommodation and/or recognition for achieving a goal or milestone through interaction with a tool enabled by this disclosure.

The term data, as it is used throughout this disclosure, is defined as facts and statistics collectable for reference and analysis, which can in some applications be stored digitally in a database or other repository. The term bucket, as it is used throughout this disclosure, is defined as a collection of data stored in a database, for example, as by providing a set of data dividable into identifiable regions or groupings.

Various aspects of the present disclosure will now be described in detail, without limitation. In the following disclosure, a threat assessment and response facilitation system will be discussed. Those of skill in the art will appreciate alternative labeling of the threat assessment and response facilitation system as a threat assessment and traumatic event mitigation platform, threat management application, response assistance system, the invention, or other similar names. Similarly, those of skill in the art will appreciate alternative labeling of the threat assessment and response facilitation system as a threat assessment and event management operation, threat assessment and response assistance method, learning and response method, method, operation, the invention, or other similar names. Skilled readers should not view the inclusion of any alternative labels as limiting in any way.

Referring now to FIGS. 1-14, the threat assessment and response facilitation system will now be discussed in more detail. The overview of the threat assessment and facilitation system will now be discussed in greater detail. FIG. 1 highlights examples of the overview of the threat assessment and facilitation system, which may also be shown in other figures.

A system enabled by this disclosure may advantageously provide multiple modules and/or components operable on a computerized device including a processor and memory to provide assistance in training professionals and/or other users to recognize potential risks of a traumatic event or violent behavior through coordination between the modules and/or components. Components may be included in separate software modules, which may be hosted on discrete systems distributed across an interconnected network, for example, the internet. In another embodiment, one or more of the modules and/or components may be operable on a common computerized device and may communicate among one another over an internal network and/or other electronic communication system.

In at least one embodiment, the components may be included on virtualized instances hosted on one or more common server computerized device. For example, virtualized instances may share resources such as processor time, memory allocation, storage allocation, and/or other allocations of resources that would be appreciated by a person of skill in the art after having the benefit of this disclosure. Additionally, skilled artisans will appreciate further configurations through which the components and/or modules included in a system or platform enabled by this disclosure may operate with one another, without limitation.

One or more of the modules discussed throughout this disclosure may be siloed with respect to other modules. For example, one or more of the modules discussed throughout this disclosure may operate substantially independently of the other modules for purposes of segregating data, permissions, access, and other characteristics over which control is desired. These modules may provide a limited selection of data to be available to other modules electronically and communicably connected to the module via established data sharing protocols. For example, information included in one module may be made accessible and retrievable by another module via an application programming interface (API). Those of skill in the art will appreciate other protocols that may be used to share data within the permitted range between modules and/or other applications, without limitation.

In some embodiments, information may also be shared with external applications and/or databases. Additionally, information may be retrieved and/or sourced from external locations and may be used to supplement the data created internally and/or be used to create derivative data sets or information usable by the modules of a system enabled by this disclosure.

Various illustrative modules includable by a system enabled by this disclosure will be discussed in the sections below with more detail. These discussions are intended to provide an illustration of how a system such as ones enabled by this disclosure may operate and is not intended to limit the scope of any invention operable in view of this disclosure in any way. Skilled artisans will appreciate variations and other implementations that will become apparent after having the benefit of this disclosure. These variations and implications are intended to be included within the scope of this disclosure, without limitation.

A system enabled by this disclosure may include multiple modules interconnected with one another via a network. For example, an illustrative system 100 may include a threat assessment assistance module 400, a learning portal module 500, a client portal module 600, a response coordination module 700, a training broker module 800, a messaging module 900, a mobile application module 920, a training evaluation module 940, and an external web application module 1000. These modules will be discussed in greater detail below. Additional modules and components may be included such as, and without limitation, an assist submission component, machine learning engine, and additional modules and components that will be discussed in greater detail below. The threat assessment and response facilitation system may operate one or more of these modules interactively with other modules for facilitating communication, assessing threats and risk of violence and divergent behavior, assessing trauma related to a public emergency such as a health crisis, and facilitating response to a traumatic event.

A system enabled by this disclosure may additionally include multiple databases linked to corresponding modules. For example, the databases may include a threat assessment assistance database 402 communicatively connected to the threat assessment assistance module 400, a learning portal module database 502 communicably connected to the learning portal module 500, a client portal database 602 communicably connected to a client portal module 600, a response coordination database 702 communicably connected to the response coordination module 700, a training broker database 802 communicably connected to the training broker module 800, a training evaluation database 942 communicably connected to the training evaluation module 940, and an external web application database 1002 communicably connected to the external web application module 1000. These databases will also be discussed in greater detail below.

In various embodiments, one or more of these above-mentioned modules and/or corresponding databases may be excluded from the final version of the application. These embodiments may be customized per application and/or deployment specifications. In additional embodiments, one or more additional modules may be provided to supplement the capacities and/or abilities of a respective system including such modules.

Figure 2:
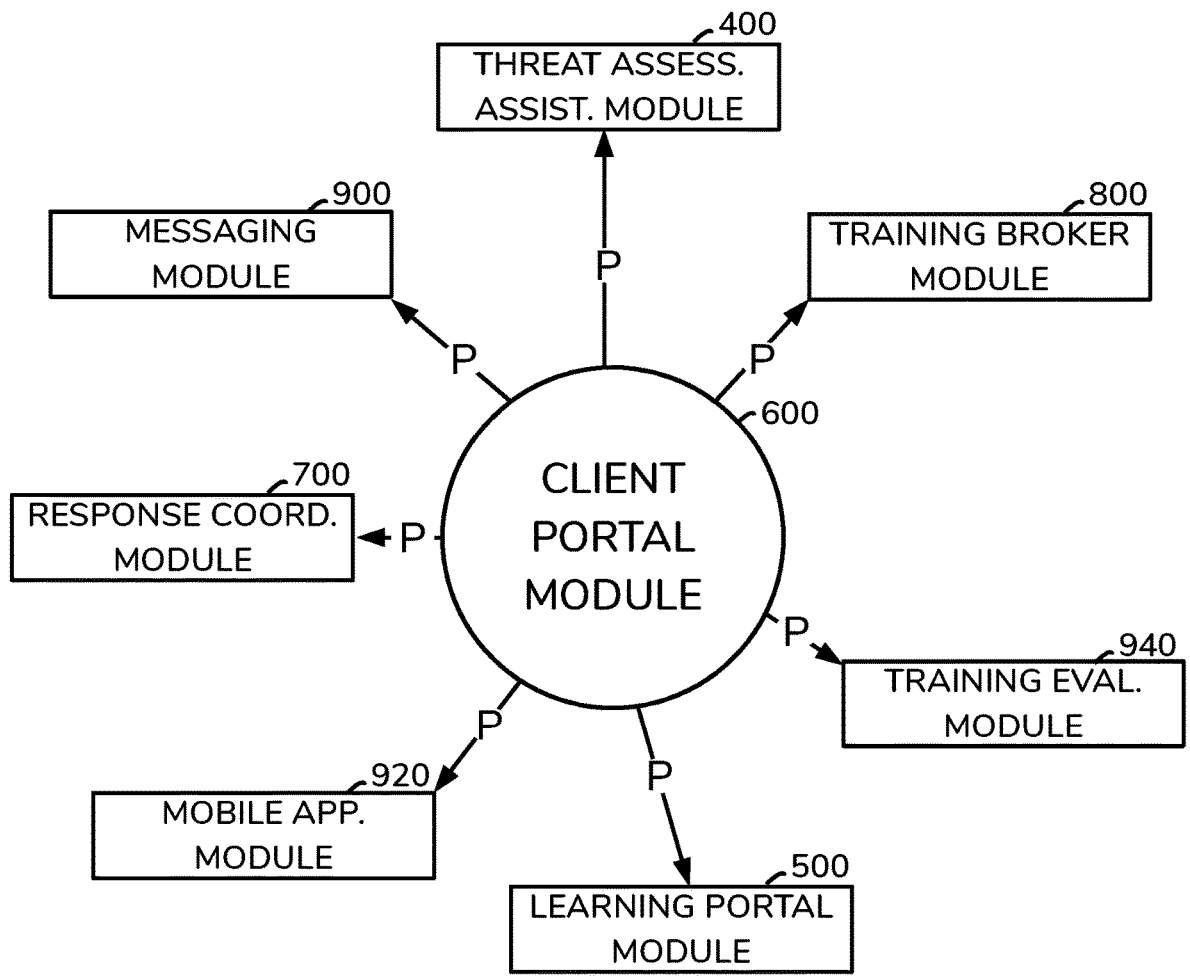
FIG. 2 is a block diagram view of an illustrative permissions structure for the modules, according to an embodiment of this disclosure.
Figure 3:
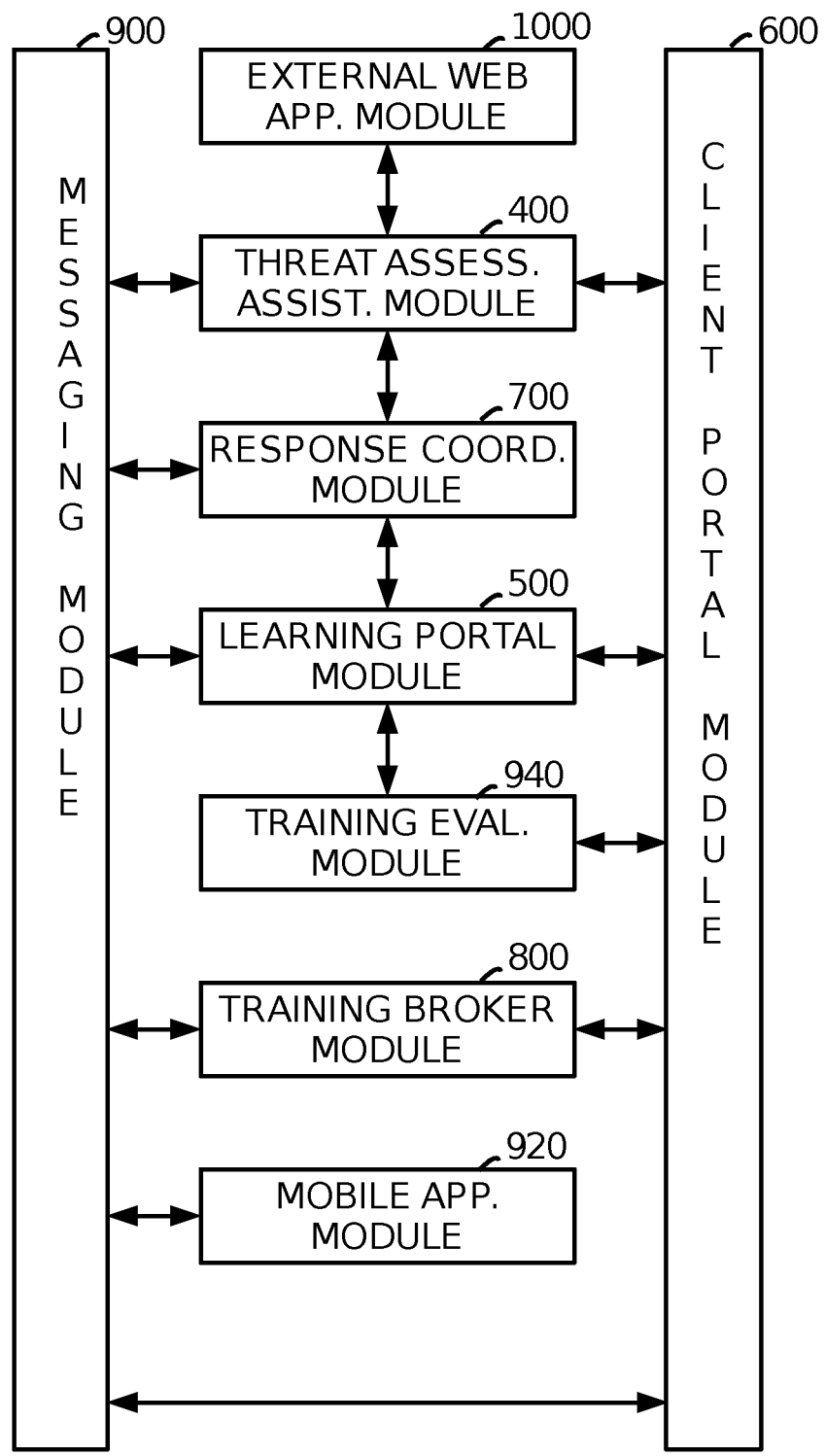
FIG. 3 is a block diagram view of an illustrative communication structure for the modules, according to an embodiment of this disclosure.
Figure 4:
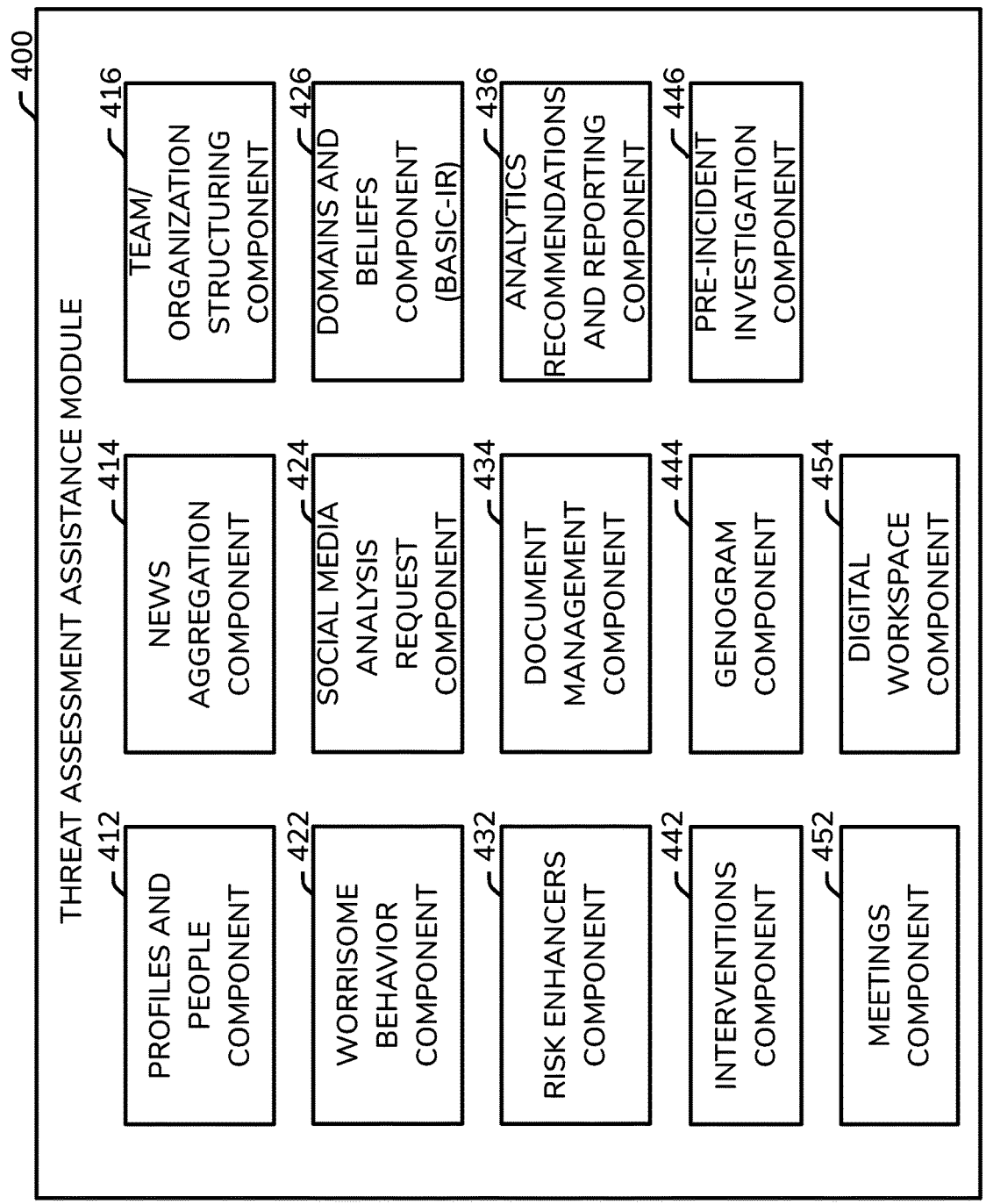
FIG. 4 is a block diagram view of an illustrative threat assessment assistance module, according to an embodiment of this disclosure.
Figure 5:
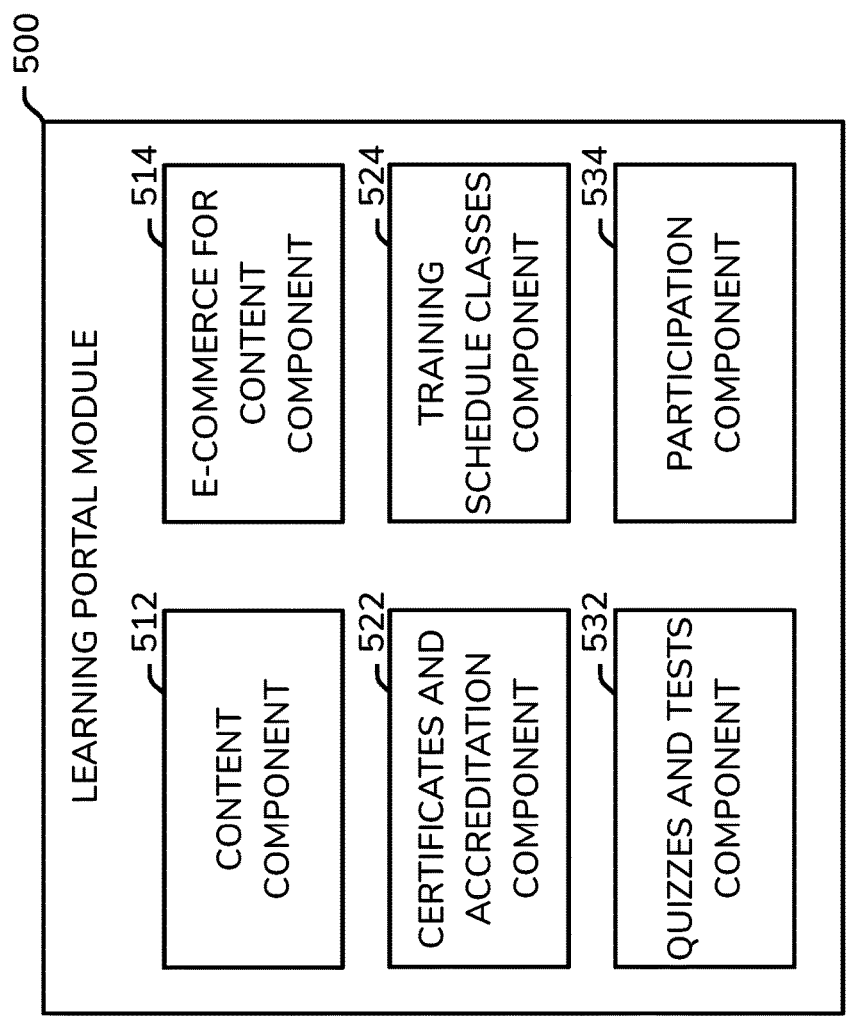
FIG. 5 is a block diagram view of an illustrative learning portal module, according to an embodiment of this disclosure.
Figure 6:
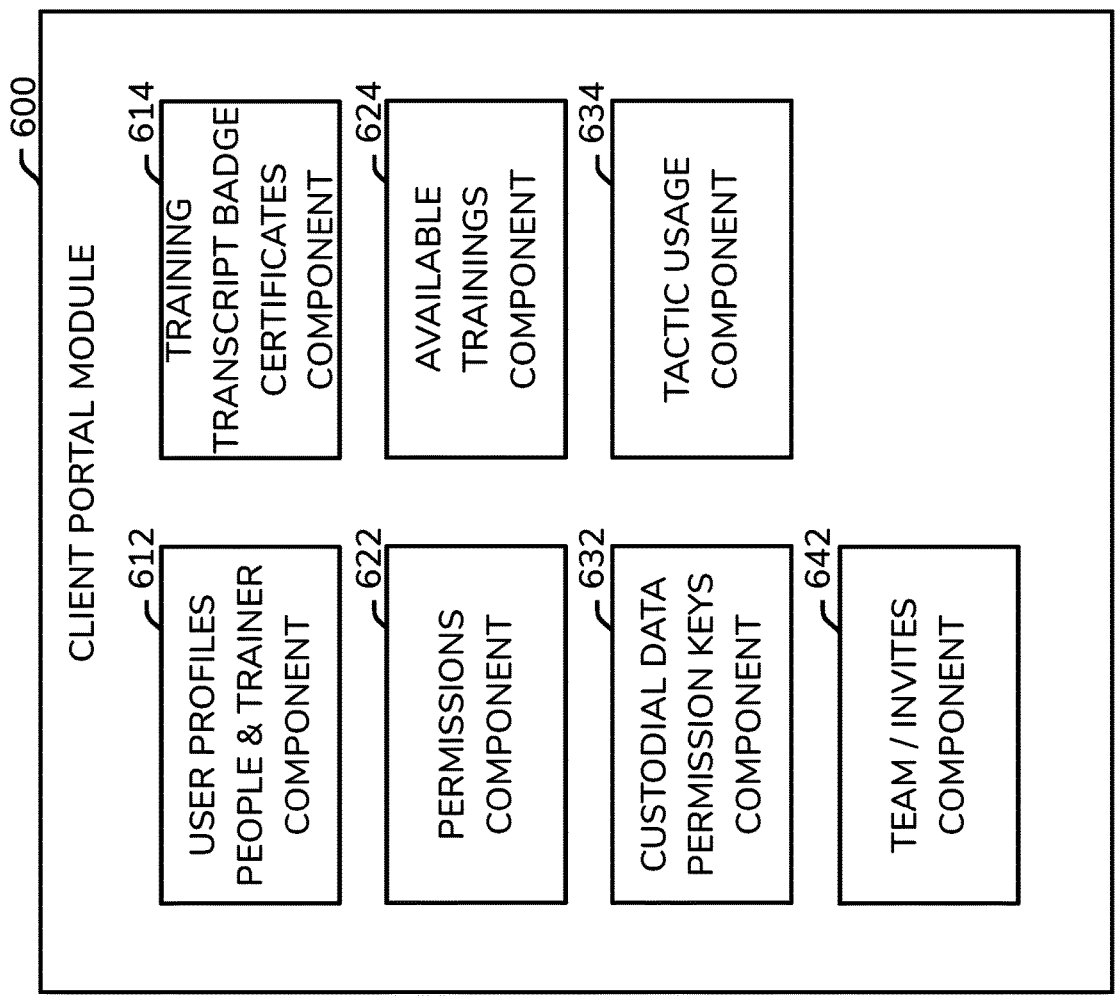
FIG. 6 is a block diagram view of an illustrative client portal module, according to an embodiment of this disclosure.
Figure 7:
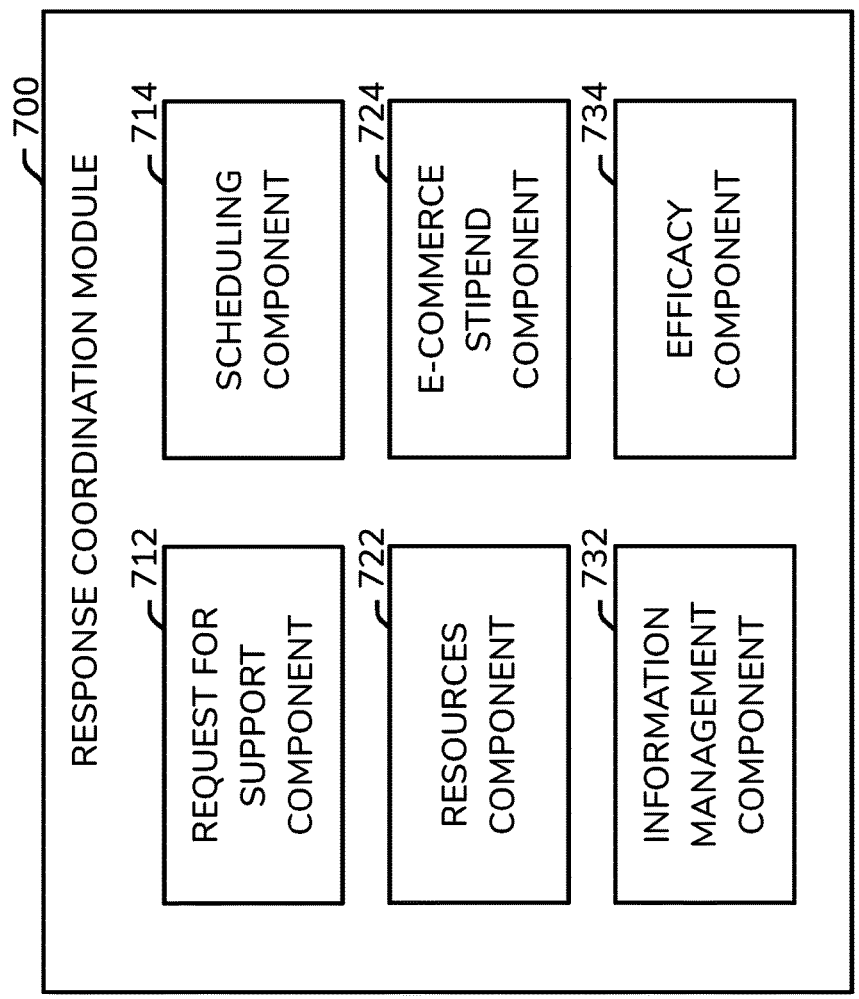
FIG. 7 is a block diagram view of an illustrative response coordination module, according to an embodiment of this disclosure.
Figure 8:
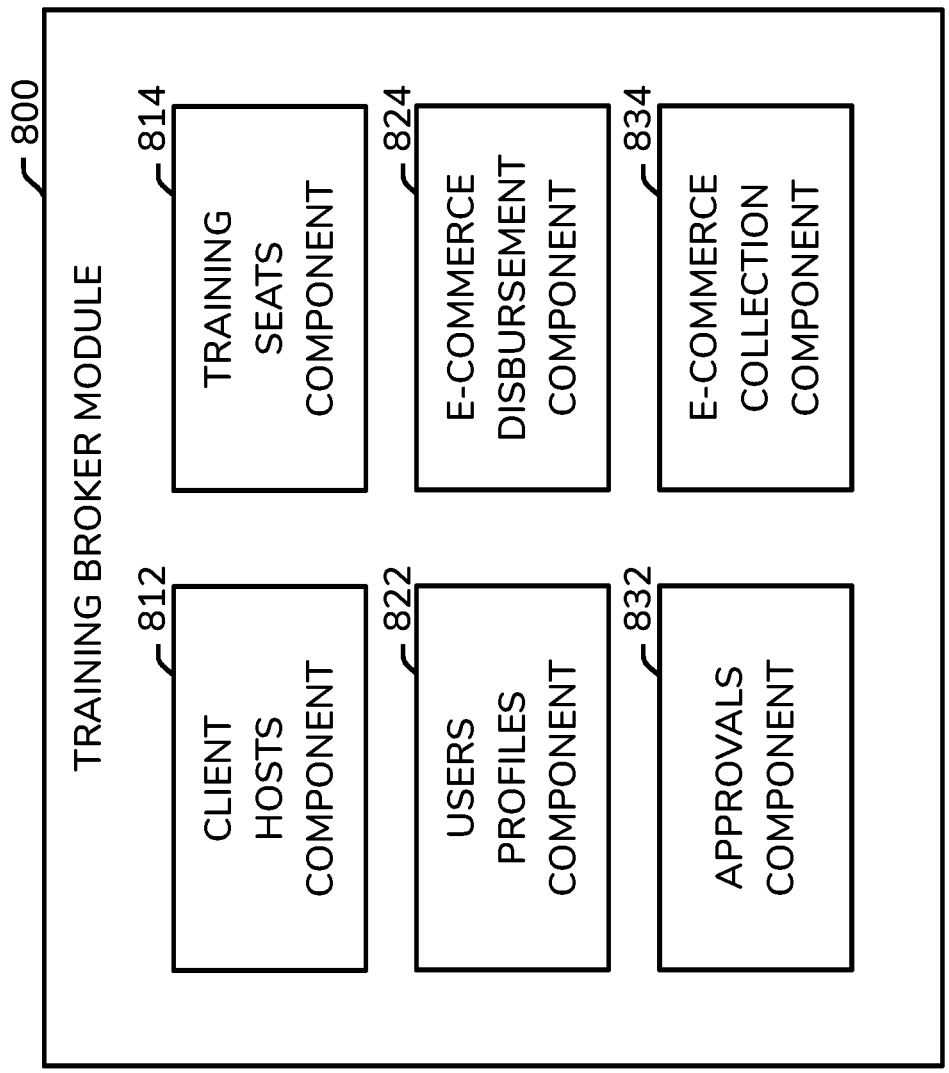
FIG. 8 is a block diagram view of an illustrative training broker module, according to an embodiment of this disclosure.
Figure 9:
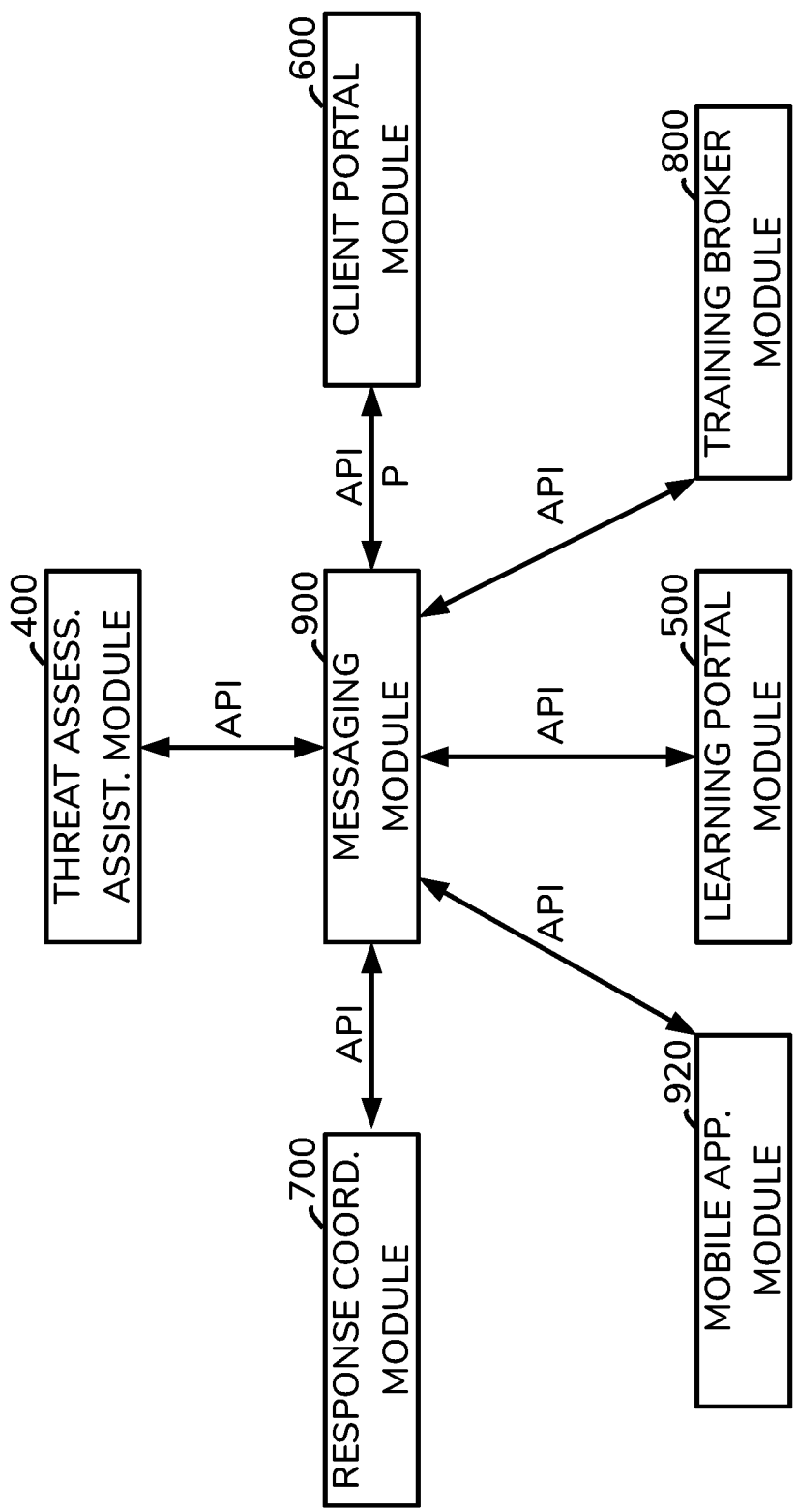
FIG. 9 is a block diagram view of an illustrative messaging module, according to an embodiment of this disclosure.
Figure 10:
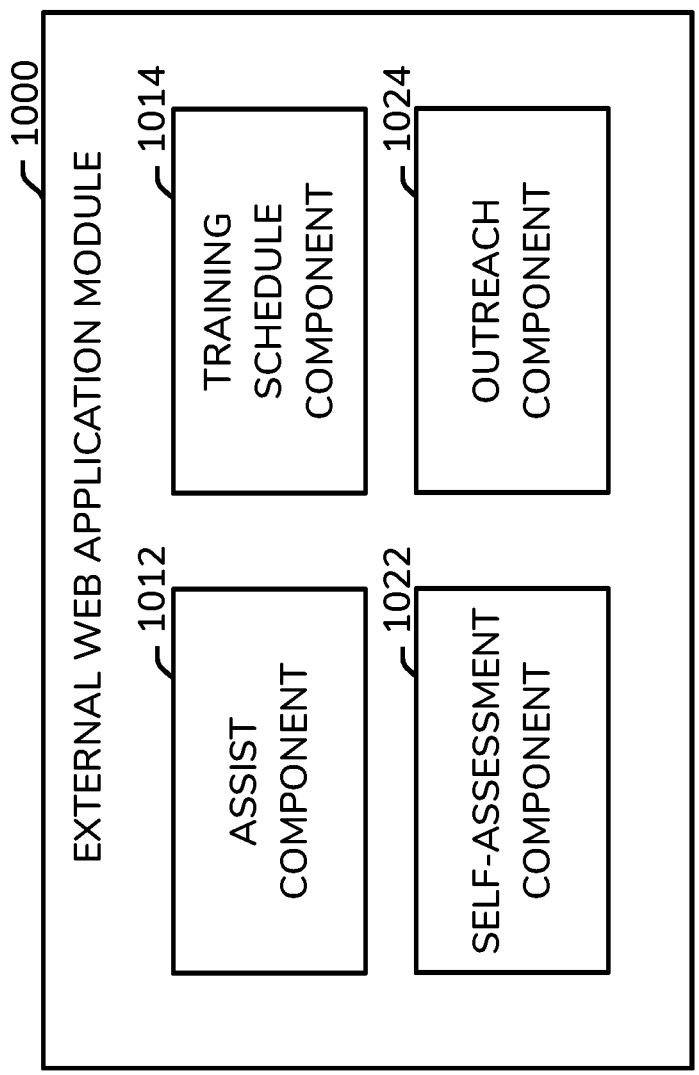
FIG. 10 is a block diagram view of an illustrative external web application module, according to an embodiment of this disclosure.

The connective structure of modules and their associated databases will now be discussed in greater detail. FIGS. 1-3 highlight examples of the connective structures, which may also be shown in other figures. The connective structure may include various modules, which may be communicably connected to other modules via communications pathways. Data relating to a module may be stored in a database associated with the module. Multiple modules may communicate with each other via API protocols defined by each module, which may control access based on permissions that can be controlled by one or more of the modules.

In one embodiment, modules may include one or more component to perform operations and transform data. The components may include computer instructions storable in memory, which may be read from the memory to be operated by a computer processor. The electronic instructions may be executed to analyze data, create derivative data based on the analysis, and detect correlations and patterns in the data otherwise undiscoverable without assistance of a system such as enabled by this disclosure.

The modules may also include a database, which may be operatively connected to one or more of the components included in the module. The database may store data relating to operation of components in the module and provide access to data to the components of the module. Data stored in a database for the module may be provided to requesting entities, for example other modules, via API.

The databases may be siloed with the module, such that the information stored by the database can be made readily accessible to the components of that module. The database may be communicably connected to the component of the module to store the at least part of the electronic instructions and data associated with the module.

Information stored in the database of the module may be made accessible to a requesting entity, such as another module, via requests handled through an application programming interface (API). For example, a module may communicate with a requesting entity having sufficient permissions at least part of the data included by the database associated with the module and to affect operation of the component included by the module, as requested and permitted via the API. In one embodiment, data stored by the database may be made selectively available to the requesting entity via the API, as governed by permissions. As mentioned above, the data stored by the database may be made directly available to the component of the module without requiring requests be made via an API.

A permissions structure may be controlled by at least one of the modules designated to manage the permissions to selectively grant access to exchange at least part of the data stored by the database of a module. The permissions may control access relating to a requested execution of at least part of the electronic instructions of the component of the module.

Data and/or execution of electronic instructions that are requested and permitted may be communicated with requesting entities via a communication structure, which may be controlled by at least one of the modules designated to manage communications. In one embodiment, the client portal module 600 may control permissions relating to communication among at least some of the modules. The communication may permit a module to selectively transfer at least part of the data included by the database of that module with another module and/or other requesting entity, as permitted by the permissions structure via the API of the module.

In one embodiment, the communication structure may provide a direct communication pathway between the modules that are directly connected via the API. For example, referring to FIG. 1, an illustrative direct pathway is shown between the threat assessment assistance module 400 and the client portal module 600.

The communication structure may additionally provide a bridged communication pathway between the modules that are indirectly connected via the API by sharing at least one intermediary module being communicably connected to the modules via the API. Referring to FIG. 1, an illustrative bridged communication pathway between modules that are indirectly connected via the API may include the threat assessment assistance module 400 communicating with the learning portal module 500 via an intermediary connection with the messaging module 900. More particularly, the threat assessment assistance module 400 may communicate data intended for the learning portal module 500 by first transmitting the data to the messaging module 900 using a first API pathway. The messaging module 900 may then determine the intended recipient of the data is the learning portal module 500, to which the messaging module 900 may relay the data received from the threat assessment assistance module 400 using a second API pathway.

Additional examples of the connective structure of modules with regard to permissions will now be discussed. FIGS. 1-3 highlight these examples of the connective structure of modules, which may also be shown in other figures. In these examples, permissions of one or more of the modules of a system enabled by this disclosure may be controlled by other modules of the system. In one embodiment, a module may be designated as a primary module to effectively control permissions of information shared between the other modules and/or components of a module. In the interest of providing a clear example of this organizational structure, the client portal module 600 will be discussed throughout this disclosure as the managing module controlling permissions for other modules. Those of skill in the art will appreciate alternative embodiments in which additional modules may include managing module capabilities and/or may control aspects of permission management, without limitation.

The client portal module 600 may be communicably connected to other modules to share information and/or control permissions including management of information sharing between such other connected modules. For example, the client portal module 600 may be communicably connected to the threat assessment assistance module 400, training broker module 800, training evaluation module 940, learning portal module 500, mobile application module 920, response coordination module 700, messaging module 900, and/or additional modules that will be appreciated by a person skilled in the art after having the benefit of this disclosure. By providing a connective structure such as the example discussed above, the primary module controlling permissions may effectively keep information segregated between the various modules to reduce the likelihood and/or prevent access of protected information included in one module from being available for other modules.

This permission management approach may be advantageous when the various modules of the system enabled by this disclosure are used by different parties with different rules for the assessment of threats and response to violent or traumatic events. For example, professionals involved in recognizing incidents and/or worrisome behaviors that may be indicative of a person of concern having an elevated threat of involvement in a traumatic event may not wish to share their information with law enforcement or other first responders that would be present on the scene in the aftermath of a violent or traumatic event. This data segregation may be necessary to preserve client-patient confidentialities, to avoid unnecessary profiling, to maintain the autonomy of the professionals involved in assessing and responding to traumatic events and acts of violence, and other reasons that would be apparent to a person of skill in the art after having the benefit of this disclosure.

In another example, personally identifiable information (PII) may need to be restricted due to regulatory and/or privacy concerns. This PII may be specified in a database into which it is stored to restrict access to only those parties with permissions sufficient to view PII. Protection of, and controlled access to, PII may be a feature of a custodial data module that may be applied to one or more component of a platform enabled by this disclosure, as will be appreciated by those of skill in the art. To assist with protection of PII, data relating to PII may be encrypted, for example, encrypted at rest.

The modules included by a system enabled by this disclosure may be communicably connected to an instance database holding information respective to the operation of that module. Each of these databases may be isolated from those of the other modules to assist with segregating the data from access between various modules without the appropriate permissions. Optionally, a global database may be included to store information made accessible to one or more of the modules included by a platform enabled by this disclosure.

For example, a threat assessment assistance module 400 may be communicably connected to a threat assessment assistance database 402, which may be a regional instance database that could include PII. In this example, the training broker module 800 may be communicably connected to a different training broker database 802. Furthermore, the learning portal module 500 may be connected to a learning portal database 502, which may be a database instance kept separate from the database instances connected to the training broker module 800, the threat assessment assistance module 400, and other modules. In some embodiments, these database instances may be physically included on a common piece of hardware, but they may be provisioned or partitioned in such a way that the information associated with one database instance is not readily readable, writable, or otherwise accessible to other database instances without the appropriate permissions.

The primary module, in this example the client portal module 600, may control not only what information is shared from this primary module to other modules, but also which information is shared among the other various modules. For example, the client portal module 600 may control which information included in a database connected to a first module may be provided to a second module. These permissions may be maintained through use of APIs or other information interfaces that would be appreciated by a person of skill in the art.

In one example, permissions may be managed to control access to information provided through various APIs related to one or more of the modules included by a system enabled by this disclosure. This permissions management may use various keys, tokens, definitions, or other forms of authentication to ensure that the module and/or user requesting access to protected information is permitted such access. Permissions management may be controlled through an interface accessible through one or more of the modules, for example, the client portal module 600. Permissions management may additionally be controlled through the backend of the platform on which the modules operate. Permissions may be added, modified, removed, controlled, and otherwise adjusted by a user in a managerial and/or administrative role, as may be defined in the deployment of a platform or system enabled by this disclosure.

The connective structure of modules with regard to API communication relationships will now be discussed in greater detail. FIGS. 1-3 highlight examples of the connective structure of modules, which may also be shown in other figures. As will be appreciated by those of skilled in the art, an application programming interface (API) is an interface or communication protocol that enables communication between various computer programs and/or modules without giving full access to the internal workings of such programs and/or modules. APIs may be provided internally within different modules of a common platform, externally over a network such as the internet, or otherwise as will be appreciated by those of skill in the art. APIs may advantageously include specifications for routines, definitions for data structures, data, information, object data, variables, and/or other useful information that can be used by other modules and/or programs connected through the APIs.

Information included in various databases associated with one or more of the modules included by a platform enabled by this disclosure may be controlled and shared through various API connections. For example, information held in a threat assessment assistance database 402, which may be a regional instance database associated with the threat assessment assistance module 400, may be managed and controlled by that threat assessment assistance module 400, with only selected information being made available for sharing with other modules connected via an API. In this example, data from the threat assessment assistance module 400 may be shared with other modules such as the response coordination module 700, messaging module 900, or client portal module 600. In another example, information included in a training broker database 802, such as a PCI database instance, connected to the training broker module 800, may be managed by the training broker module 800 such that selections of information are sharable with the messaging module 900 and/or the client portal module 600. In examples where a module is communicably connected to multiple other modules via its API, different information may be shared with each of the connected modules respective to the goals to be accomplished by the communication between these modules, which may differ from module to module.

Some modules included by a platform enabled by this disclosure may be able to receive information through a first API pathway with one module and transmit such information through a second API pathway with another module. The information received through the first pathway may be managed, processed, altered, or otherwise conditioned before being passed through the second API pathway to the second module. Some modules included by a platform enabled by this disclosure may be connected to multiple additional modules via multiple respective API pathways. Although some modules may have direct connections to other modules via dedicated API pathways, these modules may have indirect pathways to other modules via intermediate modules with API pathways between each link.

The information shared for accessing data throughout an API call may be at least partially encrypted to obscure the information from being accessed or intercepted by external applications or other modules lacking sufficient permissions. The data contained within the encrypted protocol may be accessed by a requesting module or application after validating and demonstrating sufficient permissions to receive and/or use such requested information.

To facilitate the protection of information transferred via APIs, private APIs may be used for internal communication of information between the various modules of a platform enabled by this disclosure. Additionally, partner API interfaces may be provided for communication of information between select trusted partners that may be external to the platform enabled by this disclosure, but still have sufficient trust and operational relationship requirements such that it is elevated above that of a public API access request.

An example of a partner API relationship may be a connection to a law enforcement database, news syndication database, professional regulation and credential validation database, and/or other such databases that will be apparent to a person of skill in the art after having the benefit of this disclosure. Data accessible via API may be encrypted, for example, using industry-standard encryption protocols that would be appreciated by a person of skill in the art. For example, data accessible via API may be managed via a private key and/or credentials unique key, without limitation. For other access requests, a public API key may be provided to allow access to selected information designated as being determined as being useful to the public without compromising confidentiality or the operational goals of a platform providing such data.

Referring to the example shown in FIG. 3, the messaging module 900 may include API connections with the client portal module 600, the mobile application module 920, the training broker module 800, the learning portal module 500, the response coordination module 700, and the threat assessment assistance module 400. The client portal module 600 may include API connections with the messaging module 900, the training broker module 800, the training evaluation module 940, the learning portal module 500, and the threat assessment assistance module 400. The mobile application module 920 may include an API connection with a messaging module 900.

The training broker module 800 may include an API connection to the messaging module 900 and the client portal module 600. The training evaluation module 940 may include an API connection to the client portal module 600 and the learning portal module 500. The learning portal module 500 may include an API connection with the training evaluation module 940, the messaging module 900, the client portal module 600, and the response coordination module 700.

The response coordination module 700 may include an API connection with the learning portal module 500, the threat assessment assistance module 400, and the messaging module 900. The threat assessment assistance module 400 may include an API connection with the response coordination module 700, the messaging module 900, the client portal module 600, and an external web application module 1000, if provided. Those of skill in the art will appreciate that additional API connections may be provided in different configurations of a platform enabled by this disclosure, without limitation. Additionally, one or more additional modules may be included in a platform, which may be connected to one or more of the above described modules.

The threat assessment assistance module will now be discussed in greater detail. FIGS. 1-4 highlight examples of the threat assessment assistance module 400, which may also be shown in other figures. The threat assessment assistance module 400 may be referred to throughout this disclosure as a TACTIC module, without limitation. The threat assessment assistant module 400 advantageously assists with the detection, observation, monitoring, and management of a person of concern that may have an increased risk of engaging in violent or divergent behavior. By including such a module, the parent platform may advantageously increase the fluidity in which a person of concern may be monitored to increase the safety of such person and others in contact with the person of concern.

The threat assessment assistance module 400 may advantageously assist with organization of information relating to monitoring and detecting elevated risks of a violent or divergent event by a person of concern. For the context of this disclosure, person(s) of concern includes a person, multiple independent people, or a group of people showing increased risk and/or threat characteristics both directly and/or indirectly of committing a violent or divergent act, for example as affected by environmental and societal influences.

The threat assessment assistance module 400 may assist with detecting a threat to others by a person of concern. The threat assessment assistance module 400 may additionally help with detection of a risk to the self from a person of concern. For example, the threat assessment assistance module 400 may assist with identifying signs of potential future violence to the self and others, including risk and threats of suicide, homicide, battery, assault, fighting, targeted attacks, or other highly undesirable events that could result in the harm of members of our society. Tools provided through the threat assessment assistant module 400 and other modules of a platform enabled by this disclosure may advantageously apply to school settings, workplace settings, organizational groups, business settings, and other settings where people of multiple groups may gather and interact with one another.

Unlike previous unidimensional techniques used in the detection of threats, such as preparing surveys and manually and individually analyzing the results to such surveys, the threat assessment assistance module 400 advantageously provides an interactive and analytical platform to use information to aid in the assistance of predicting potential risks and outcomes from such information. The threat assessment assistance module 400 may advantageously benefit from a novel multiple disciplinary collaboration between multiple users and professionals with differing and/or complimentary perspectives, allowing information to be easily aggregated and analyzed to produce more useful results.

Machine learning, such as may be provided by a machine learning engine, may be applied to the information received through the threat assessment assistance module 400 to assist with detecting patterns and identifying correlations between stimuli and reactive events. By using modules such as the threat assessment assistance module 400, multiple disciplinary professionals may decrease the likelihood that managing large sets of information will become overwhelming and resulting diminished utility from the overwhelmed analysis inherent to a disfavored unidimensional approach. Additionally, inclusion of machine learning operations may assist with the management of information over time, detecting patterns and trends relating to same, and providing temporal insight otherwise impossible without the beneficial insight provided via the machine learning engine. Modules such as the threat assessment assistance module 400 may additionally help manage the workflow of retrieving information from a set of events and other conditions by partitioning a workflow into manageable steps that may be performed by professionals spanning multiple disciplines and/or computerized devices. Those of skill in the art will appreciate that some tasks will be too complex to be mentally performed by a human operator and will require completion by a computerized device such as one operating a platform or system enabled by this disclosure.

The threat assessment assistance module 400 may require users to login prior to receiving access to the features of this module, such as via interaction with a login screen. The login screen may be displayed to the user through a connected module, such as the client portal module 600 and/or the mobile application module 920. The login of a user may control permissions available to the user to access other content that may be provided by a system enabled by this disclosure.

The threat assessment assistance module 400 may provide a dashboard interface to authorized users to display information relating to operation of a system enabled by this disclosure, such as for quickly viewing information regarding one or more person of concern. The dashboard screen may be displayed to the user through a connected module, such as the client portal module 600 and/or the mobile application module 920.

The threat assessment assistance module 400 may include analytic operations such as semantic mapping. These analytic operations may be assisted by machine learning, such as may be provided by the machine learning engine. Semantic mapping operations may assist with using natural language to detect patterns and triggers, which may help with determining whether a follow-up could be beneficial. The semantic mapping operations may also allow identifying slang and target words that may be otherwise unknown to the assessing professional. The semantic mapping operation may otherwise assist with associating information gathered by the professional with a global knowledge base to help interpret this information into derived knowledge and information that is more useful.

In one example of semantic mapping, a session with a person of concern may include discussion about "speeding." Without proper training or exposure to the term, a professional administrating the evaluation may assume that references to "speeding" has to do with driving at an excessive speed in a motor vehicle. However, slang terms may have evolved to give this "speeding" term an underground or informal meaning.

In this example, an underground meaning for the term "speeding" may include consuming methamphetamine or other state-of-mind altering substances. In previous procedures for analytical operations, an administering professional would likely remain unaware of this slang term and may miss this potential trigger. However, with the benefit of the threat assessment assistance tool and other tools provided through a platform such as the one described throughout this disclosure, the correlation between the slang term "speeding" and an increased use of a state-of-mind altering substance can be made whether or not the administering professional is aware such a correlation exists. This correlation may additionally be included in a person of concern profile associated with the person of concern, as will be discussed in greater detail below. Those of skill in the art will appreciate additional examples of terms that may be analyzed via semantic mapping that are associated with violence and divergent behavior, such as "chads," "staceys," "plug," "toys", "spinners", "mashers", "burners," "wooshing," "duppying," and other phrases subject for semantic mapping, without limitation.

One example of the threat assessment assistance module 400 may include a profiles and people component 412, news aggregation component 414, team organization and structuring component 416, worrisome behavior component 422, social media analysis request component 424, domains and beliefs component 426 (shown as BASIC-IR representing behavioral, affective, somatic, interpersonal, cognitive, ideology, and religiosity domains), risk enhancers component 432, document management component 434, analytics recommendation reporting component 436, interventions component 442, genogram component 444, pre-incident investigations component 446, and/or one or more additional components that would be appreciated by a person of skill in the art after having the benefit of this disclosure. These above-mentioned components may collectively include information managed through custodial data permissions (CDP). As seen and FIG. 4, multiple components included within this illustrative threat assessment assistance module 400 may additionally benefit from natural language systems, including those leveraging machine learning and pattern recognition.

The profiles and people component 412 may be included as a point of reference for an observed person, which may include persons of concern, witnesses, victims, targets, and/or those being observed for potential of violent or divergent behavior. A person of concern may be identified using a custodial data model, in which information about the person of concern is maintained by a custodian of the data relating to the person of concern. Those having skill in the art will appreciate that persons monitored by the profiles and people component 412 may include persons of concern, witnesses, targets, potential victims, potential victim groups (for example, persons with black hair and brown eyes), past victims, and others that may present a shift in a baseline in behavior. For the purpose of this disclosure, a baseline behavior is defined as a behavior that is typical to an individual and/or group. If behavior is detected that is a deviation from a previously defined baseline behavior or otherwise not typical behavior, evolution of a person and/or group towards violence or other threats may be inferred. The persons monitored through the profiles and people component 412 may be observed to indicate a change in their baseline and assist in assessing what stimuli may have influenced such a shift.

Changes in the baseline behavior may related to fluidity—the interaction between the suicidal and homicidal domains. Fluidity may be most common in individuals experiencing intense emotional pain, which may cycle through periods of wanting to kill themselves and periods of wanting to kill others. When the suicidal and homicidal domains start to interact with each other, fluidity may occur where the person of concern may begin to struggle with whether or not to kill or harm themselves, someone else, groups of other people, or a combination of these targets. Recognition and consideration of fluidity when assessing a threat and/or risk is advantageous, as additional context may be given to the struggles being experienced by a person of concern as the homicide/suicide continuum may fluctuate between a cry for help and an intent to harm oneself or others.

Profiles relating to a person of concern may include tags, which may provide users with a quick reference to information included by the profile for a person of concern. A human team may view these tags, modify these tags, and/or use these tags to assist with deciding a recourse, if any. Self-assessment may be given by a person of concern, which may additionally be used to generate tags, information to be associated with that person of concern, and other information to assist with the assessment of threat and/or risk relating to the person of concern.

In some examples, custodial data may include personally identifiable information (PII). In some embodiments, consent may be required before such information may be collected regarding a person. Permissions may be controlled for which selection of information relating to a person of concern is viewable, shareable, or otherwise accessible by users of a platform enabled by this disclosure. In some instances, cases and information from the profiles of multiple persons of concern may be anonymized for sharing with researchers, creation of case studies, or production of other materials and information that may assist with mitigating future violent events or improving conditions that may otherwise increase risk of such events occurring. Additional examples of data that may be encrypted can include, without limitation, social security numbers, credit card numbers, financial account information, medical record information, and other data that may include sensitive and/or confidential information that could be used to identify a person and/or group. For the purpose of this disclosure, anonymizing is intended to include removal of substantially all, if not all, identifying information about the person for which the data was created.

Anonymized data and other data, for example data including PII, may be encrypted. Those of skill in the art will appreciate various encryption protocols and techniques that may be applied to data, which is intended to be included within the scope of this disclosure. Data may be encrypted at rest, which may provide encryption of data when it is being stored in a computer readable medium such as a database, bucket, flat file, or memory. The data may additionally be encrypted in process, which may provide encryption of active data in a non-persistent digital state, such as when being stored in volatile memory. Additionally, data may be encrypted in transit, including when data is being communicated between databases, modules, systems, outside requests, via API calls and posts, and otherwise moved from one electronic component to another.

Data encryption may include a reference key, which may be associated with data to be protected via the encryption. A shared key may be provided to a party desiring to access and use the encrypted data. Additional classifications of keys may be used, including shared keys, private keys, credential-unique keys, and other keys that would be appreciated by a person of skill in the art after having the benefit of this disclosure.

Encryption may be provided in various levels, which may be determined to match a vendor and/or operator needs. Encryption levels, including key sizes being a number of bits in a key used by a cryptographic algorithm to access the information included by the encrypted data, may also be determined based on the level of security needed to protect information provided by the data, which could be based on the nature and/or sensitivity of the information. Encryption levels may advantageously use 512-bit encryption, without limitation. Other data may use other levels of encryption, for example, 128-bit, 256-bit, 1024-bit, 2048-bit and/or other levels of encryption that would be appreciated by a person of skill in the art after having the benefit of this disclosure. Encrypted data may include hashes, which may be salted. Keys may also be symmetric and/or asymmetric, without limitation.

By use of anonymized data in research, users of such a platform may advantageously derive trends indicative of risk, violence, and societal disconnects that may affect the mental state of a person of concern and increased the likelihood that a violent event may occur. This analysis of anonymized information may be assisted by machine learning, which may employ a computerized device to analyze a high volume of data with the goal of detecting patterns and correlations to assist with predicting future outcomes for a set of stimuli or influences. The analysis of data by a computerized device may exceed the capabilities of a human operator, adding additional utility to a system enabled by this disclosure. Those of skill in the art will appreciate machine learning techniques that may be applied to enhancing the interpretation of anonymized data and information to extra patterns and supplement the knowledgebase available to users and professionals, which is intended to be included within the scope of this disclosure.

Management screens associated with the profiles and people component 412 may be displayed to the user through a connected module, such as the client portal module 600 and/or the mobile application module 920. Information about a person of concern may be collected, recorded, analyzed, and optionally shared with additional parties such as incompliance with the custodial data permissions (CDP). Profile information may include history of incidents, prior events occurrences that could influence the behavior of the person of concern, and/or other behavioral information that may be relevant to understanding factors that may affect the behavior of the person of concern.

The news aggregation component 414 may be included to aggregate information relating to an environment that may affect a person of concern, events that may occur in the lives of a person of concern, adverse childhood experiences of the person of concern, events that may occur in an environment including multiple persons of concern, and/or other information that may affect the behavioral patterns of individuals and/or a societal group. The news aggregation component 414 may gather information about a past or presently occurring violent or divergent event, such as a school shooting or other act of violence. The news may include information about the perpetrator of the violent event, associates of the perpetrator, triggers that may have influenced the perpetrator to commit the violent act, victims of the act, and other information that could lead towards a change in mental state-of-mind or perception in a person of concern, other persons affected by the event, victims, and others. Reminders may be provided for critical periods relating to an event, for example and without limitation, annual reminders and/or reminders for other periods.

For example, the news aggregation component 414 may monitor reports for acts of violence or divergent behavior committed by a person of concern. Initially, the news aggregation component 414 may aggregate the names of victims and persons involved in a violent act, for example a school shooting. Persons that appear to have an elevated risk of being influenced by such an act may be tagged by other components in the threat assessment assistance module 400, such as the incidents and worrisome behavior component 422, without limitation.

In some cases, these tagged persons of concern and/or other persons subject to threat assessment may be flagged for revenge-seeking behavior or other behavior that may be at risk of perpetuating violence. In this example, the news aggregation component 414 may identify victims of a school shooting event and the profile of the perpetrator of such an event.

The news aggregation component 414 may extract information about the race or other characteristic of the perpetrator, associates of the perpetrator, and other information that may be used by a person of concern seeking revenge in a follow-up violent act. Ideally, any planning or preparation for a retaliatory event can be detected prior to its occurrence. However, should a retaliatory violent event occur by a person of concern showing a revenge-seeking bias, correlations relating to such a retaliatory violent event may be drawn to help identify potential future risks of concern, possible counseling or other diversionary programs that may reduce the risk of this person a concern committing future acts, and identifying trends relating to an environment in which a violent act has previously occurred that could lead to other individuals or persons of concern committing similar and/or retaliatory acts of violence.

In one embodiment, threat assessment may be complimented using micro and macro threat assessment models. For example, threats may be assessed using a micro assessment model, for example, determining if a threat maker poses an actual risk to carry out the current threat. Threats may also be assessed using a macro assessment model, for example, focusing on historical and foundational risk enhancers that may be contributing to overall levels of risk.

A team organization and structuring component 416 may be included by the threat assessment assistance module 400 to help coordinate the assessment of risk relating to a person of concern. The team structuring protocols may assist with the organization and allocation of resources for professionals, administrators, law enforcement, and other individuals to help predict the occurrence of a violent event and seek to diffuse such risk through intervention, counseling, and other proactive steps to de-escalate the environment catalyst that may otherwise lead a person of concern into the consideration of committing a violent act if untreated.

Professionals included in a group organization structure through the team organization and structuring component 416 of the threat assessment assistance module 400 may communicate with one another through additional modules, such as the messaging module 900. As mentioned previously, the messaging module 900 may communicate with aspects of the threat assessment assistance module 400 through the sharing of data via application programming interfaces (APIs). Those having skill in the art will appreciate additional data transmission and sharing techniques after having the benefit of this disclosure that may be used in alternative embodiments.

Professionals and other users may access information designated as being within their permissions to view and interact with this permitted data through an associated client portal module 600, which may communicate with the threat assessment assistance module 400 via an API. Additionally, information included in the team organization and structuring component 416 of the threat assessment assistance module 400 may advantageously be retrieved and leveraged by additional modules of a system enabled by this disclosure, such as the response coordination module 700, to help with the response should a violent event occur.

A worrisome behavior component 422 may be included for monitoring incidents and worrisome behavior associated with the person of concern. The worrisome behavior component 422 may assist with managing information relating to prior incidents and/or worrisome behavior that may indicate the risk of a future escalated incident. Incident management screens may be displayed to the user through a connected module, such as the client portal module 600 and/or the mobile application module 920.

Information included in the worrisome behavior component 422 may be sourced from users of the platform, sources such as the news aggregation component 414, and/or other sources that would be appreciated by a person of skill in the art after having the benefit of this disclosure. In some embodiments, the worrisome behavior component 422 may be pre-populated with common triggers indicative of a possible future violent event occurrence. This list may be dynamic, allowing addition of new incidents or behaviors viewed to be relevant to a person of concern or possible risk of future events of violence.

In one example, the worrisome behavior component 422 may include information relating to bullying or fighting between students in a school environment. An interface including an incident and worrisome behavior screen may be displayed to the user through a connected module, such as the client portal module 600 and/or the mobile application module 920.

The worrisome behavior component 422 may assist in detection of a change in behavior compared to a baseline behavior, such as an increase with regard to the baseline. In one example, an incidence of a fight, a report to the principal's office or other administrative office of bullying or other harassing behavior, teacher reports, school psychologist reports, and other information may be included in this component to help create a more complete picture of the persons of concern involved. This profile of incidents and worrisome behavior may include the student committing an act of bullying or instigating fights. These events may increase the association of the monitored person as a person that demonstrates an increasing baseline, which may relate to violent tendencies, a person acting out perhaps due to an external stimulus, or other indications worthy of follow up.

The worrisome behavior component 422 may additionally include information about baseline indicators. To illustrate one example of baseline indicators, facts relating to the victim of the bullying may be assessed, for example, frequency of such events, observations by administrators or faculty, external influences on the individual, social isolation, disconnection from others, or other divergent behavior that may be indicative of a risk or threat of future retaliatory, violent, or otherwise divergent behavior as a result the being victimized. Those of skill in the art will appreciate that the above scenarios are given as examples to clearly communicate a possible use of a platform enabled by this disclosure, without limiting the functional capacity of such a platform to only these examples.

Threat and/or risk assessment of a person of concern may be categorized to easily convey the stage of the target for monitoring and/or follow-up engagement. Categorization may include, for example, low, moderate, and high levels of concern. An example of a low categorization of risk and/or threat of trauma may indicate that an individual is that little risk for violence and monitoring may be appropriate for response. A low risk categorization may not indicate that the monitored individual is at no risk for violent in slash or divergent behavior, but such categorization may indicate that the individual being monitored remains within an acceptable variation and/or frequency of the baseline.

Categorization of moderate levels of concern may indicate that an individual is at an elevated risk for violence and measures mean need to be put in place to manage the individual's future risk. With a moderate level of concern, a threat is more plausible than with a low-level threat. However, a person showing a moderate level of concern likely shows no clear indication that the person of concern has taken preparatory steps towards committing a violent and/or divergent event. A moderate level of concern may be reflective of an increase in baseline behavior in the person of concern.

Categorization of a high level of concern may indicate that a person is at high or imminent risk for violence and immediate intervention may be required to prevent an act of violence from occurring. In persons categorized with a high level of concern, the threat of a violent and/or divergent event may be discernable and plausible. Information may suggest that the person of concern has taken steps towards acting on a threat such as by acquiring a weapon, by planning a discernable attack, or by otherwise furthering a violent and/or divergent agenda. For example, a discernable attack may include details about how such an attack would be carried out, how it will be performed, who will be targeted, and/or other details relation to perpetuating the attack. Information relating to a person of a high level of concern may strongly suggest a significant increase in baseline behavior.

By monitoring baseline indicators, information relating to incidents and worrisome behavior may be discovered including a fluidity of suicide-to-homicide variation, change in the baseline behavior of an observed person, a derived behavior relating to additional factors observed via the threat assessment assistance module 400, and/or other interactions between the suicidal and homicidal domains. For the purpose of this disclosure, fluidity is intended to include interactions between the suicidal and the homicidal domains, such as including transitions between intense emotional pain relating to periods of wanting to kill oneself and periods of wanting to kill others, the convergence between such periods, and the struggles in a person of concern between the suicidal domain, the homicidal domain, or a combination of elements from suicidal and homicidal domains.

Those having skill in the art will appreciate numerous additional examples of how such a platform may be applied to detect an elevated risk in persons of interest, properly categorize a possible incident, detect and log worrisome behaviors, and assist in recognition of patterns that may indicate the risk of a future violent or otherwise divergent event in the effort to diffuse such event before it may occur.

A social media analysis request component 424 may be included in the threat assessment assistance module 400 to request monitoring of online activity by a person of concern or others that may be connected to a person of concern by an external entity. The social media analysis request component 424 may communicate with a third-party data reporting service that monitors social media network activity of the person of concern. Third-party data reporting services may communicate with the social media analysis request component 424 via the API.

In one example, the social media analysis request component 424 may request a service, provider, and/or governmental entity to monitor social media platforms and other public forums to detect language or messaging indicative of violent behavior or the proclivity to commit the same. In another example, the social media analysis request component 424 may request another party to monitor social media platforms and other public forums to detect a change in engagement, atypical behavior, or other indicators that may suggest a change in the person of concern and how they interact with others in society.

Information gathered by the party monitoring social media accounts may be submitted or provided to a platform enabled by this disclosure via an API communication connection, a report, via a company protocol, and/or other connection that will be appreciated by those of skill in the art after having the benefit of this disclosure. Pattern matching may be applied to monitored social media accounts and information received by third parties relating to same to assess the threat and/or risk of violent or divergent behavior.

In one example, a person of concern may be monitored by a third party for their posting on social media networks. The postings may relate to friendly exchanges between the person of concern and their friends. However, in this example, it may be relevant that the person of concern disengages with their friends to an extent that is noticed and commented to by their friends. For instance, friends of the person of concern may attempt to reach out to the person of concern to ask how they are doing, where they have gone, if everything is okay, or demonstrate other expressions of concern or notice of atypical behavior. These changes to present personality and behavior may be indicative of future behaviors that would raise worry or concern. Information included by the social media analysis request component 424 may be shared with other components of the threat assessment assistance module 400, such as the worrisome behavior component 422, to give a more complete picture of risk posed by a person of concern to commit a violent or divergent act.

In one embodiment, the domains and beliefs component 426 (shown as BASIC-IR) may assist in the assessment of threat by considering domain-focused factors and belief-focused factors. The domains and beliefs component may assess a change in domain-focused factors and a change in belief-focused factors indicative of a change in behavior of the person of concern. For example, domain-focused factors may include a behavioral domain, affective domain, somatic domain, interpersonal domain, cognitive domain, and/or other domains that would be apparent to a person of skill in the art after having the benefit of this disclosure.

The behavioral domain may be relative to a shift in behavior of a target. The affective domain may be relative to a shift in the emotions of a target. The somatic domain may be relative to a shift to somatic responses, such as headaches, pain, and other ailments relating to the body. The interpersonal domain may be relative to a shift in relationship systems, such as breakup with a friend or significant other and/or associating with someone new.

The cognitive domain may relate to shifts in a person's thinking of the world around them, such as with disassociation and/or disconnection from the real world. Regarding the belief-focused factors, the ideological domain may relate to ideas and ideals, especially such that may form the basis of a perspective taken by a target of shifting ideologies. Additionally, the religiosity domain may relate to religious feelings and/or beliefs, with threat assessments considering change to such feelings or beliefs.

A risk enhancer component 432 may be included in the threat assessment assistance module 400 to detect and log information that suggests an elevated risk of the violent or divergent behavior in a person of concern. The risk enhancers component 432 may monitor conditions affecting risk of harm to the person of concern and others. A risk enhancer interface may be displayed to the user through a connected module, such as the client portal module 600 and/or the mobile application module 920.

Risk enhancers may correlate with incidents or worrisome behavior logged in other components of the threat assessment assistance module 400 or other modules included by a platform enabled by this disclosure. Risk enhancer information may include exposure to prior violent events, disruption in a home environment, moving, association with others that show a risk of concerning behavior, notions of familial abuse, domestic violence, life-altering events, major life events, and other events that may not necessarily cause a violent behavior, but may enhance the risk of violent behavior occurring when combined with other catalysts or triggers. A risk enhancer history may be maintained, which may include information relating to prior interventions, ongoing interventions, effectiveness of interventions, work performed in furtherance of the interventions, and other information relating to enhancement of risks and steps to assess and mitigate same.

An example of a risk enhancer may include temporal storage around an incident. In this example, interactions may be different between different people and different groups of people in the aftermath of an incident. The temporal component may consider days or weeks after the occurrence of an incident, such as a violent incident including a shooting or other serious harm to others, or on the anniversary of such an incident, without limitation. Those having skill in the art will appreciate other temporal milestones and periods of significance that may affect the level of risk associated with a location and incidence of a violent act. Skilled artisans will additionally appreciate that assessment of risk enhancers is not limited to shooting-based events or violent events related to mass-killing scenarios.

For example, temporal storage may be considered when analyzing the risk of a violent act on the anniversary of a proceeding violent act at a location. In a more specific example, the risk of the future violent act may be elevated on the anniversary of a previous school shooting of high notoriety and the news cycle. Additional sensitivity may be given to the analysis of potential threats and observation of persons of concern during periods of elevated risk due to temporal storage of the impact of a preceding violent incident.

A document management component 434 may be included in the threat assessment assistance module 400 to help aggregate and collect documents relating to the operations of other components in the module. The document management component 434 may additionally include documents and documentation of information collected through other modules of a platform enabled by this disclosure, without limitation. Documents may be tagged with topics included within the document, flagged for inclusion of information relevant to the analysis of other components and modules of the system, and otherwise stored for sharing and decimation between professionals and other users to assist with managing and interpreting risk, behavior, and other information relating to persons of concern.

As with other information included by the threat assessment assistance module 400, copies of the documents managed by the document management component 434 may be included in a relational instance database or other database operatively connected to the module, such as the threat assessment assistance database 402. Information included within the documents, the documents themselves, and other access and permissions may be controlled through various API connections and calls, and permissions management handled internally and/or through other modules of a system enabled by this disclosure. In one embodiment, documents may be included in storage systems that differ from traditional database storage, such as buckets stored on a remote hosting system, for example, S3 buckets hosted by Amazon web services (AWS). For the purpose of this disclosure, buckets are intended to be included in the scope of databases for storing information relating to a module.

An analytics recommendation reporting component 436 may assist with interpretation of information provided through the other components of the threat assessment assistance module 400 to determine a recommendation of follow-up monitoring or other actions. The analytics component may analyze information relating to the person of concern to maintain a record and recommend activity corresponding with the record. The record may be stored in at least part of the threat assessment assistance database 402. The analytics may include parsing information in the other components included by this module to extract information relating to risk and the assessment of the state-of-mind of a person of concern.

These analytics may be assisted by users, other modules, machine learning, and/or other tools to help increase the accuracy of the analysis and improve predictions from the analysis. The analysis may be used to assist with recommending a follow-up action, such as monitoring a person of concern more closely or intervening with the person of concern having a heightened risk characteristic. Reporting may additionally be included for those at high risk or otherwise to involve outside professionals such as psychologists or law enforcement to intervene in view of the results of the analysis and recommendations provided by the analytics recommendations and reporting component 436, without limitation.

An interventions component 442 may be provided to assist with conducting and logging information relating to intervention with a person of concern having a level of risk indicative of benefiting from such an intervention. The intervention component 442 may include information relating to the intervening parties, the response of the person of concern to the intervention, topics discussed during the intervention, and other information relating to those intervening with the person of concern. Notably, in the context of this disclosure, intervention does not exclusively include having users or other persons interact with a person of concern to explicitly discuss a detected elevated risk of divergent behavior. Intervention may initially include passively diffusing a situation that may be causing an escalation of risk in a person of concern, intervening with third parties or others that may be contributing to the risk elevation, or otherwise affecting at least part of the environment that may be contributing to a change in the behavioral patterns or increase in divergent incidents committed by the person of concern.

The genogram component 444 may be included to provide an illustrative representation of the data included by the other components of the threat assessment assistance module 400. The genogram component 444 may organize information relating to familial organization including genealogy and the worrisome behavior associated with a family member of the person of concern. Information provided by the genogram component 444 may be analyzed by the threat assessment assistance module 400 to derive insight relating to the person of concern. The genogram component 444 may advantageously assist with quickly conveying concepts of risk, environment, and other factors that could contribute to the occurrence of a violent event or other divergent behavior.

The genogram may include a graphical representation of a family tree including information about the relationships with the person of concern. In some embodiments, the genogram may include associations with friends, social groups, online social media groups, and other categorizable groups that may affect the behavior and mental state of a person of concern. Genograms may advantageously allow a therapist, psychologist, or other user of the platform enabled by this disclosure to quickly identify and understand patterns in the person of concerns relationship with family members, groups, or others that may affect the behavior of the person of concern.

In one example, a genogram may be created by the genogram component 444 of a threat assessment assistance module 400 to include information about the person of concern's family relative to the assessment of worrisome behavior, a threat, or other divergent behavior. The genogram component 444 of the threat assessment assistance module 440 advantageously provides a genogram product that assist with the detection of worrisome behavior that improves upon standard or generic genograms, assisting the other components of the threat assessment assistance component 440 with detecting a threat, identifying worrisome behavior, or otherwise organizing information relating to a person of concern.

Information includable by an illustrative genogram component 444 may include names, genders, dates of birth, dates of death, another standard information. In this example, the genogram may additionally include additional data such as education, occupation, life events, social behaviors, political affiliations, emotional relationships, illnesses, nature of family relationships between other members presented in the genogram, and other information indicative of the relationship between a person of concern and others in which the person of concern may have contact. The genograms may additionally include information relating to disorders or other conditions and that may affect the stability of the mental state of the person of concern such as alcoholism, disease, alliances, depression, living conditions, or association with groups identified as having extreme viewpoints. This information may be organized in such a way that it may be quickly digested by professionals and other users of the platform enabled by this disclosure to assess the risk of a person of concern committing a divergent or violent act and assist with diffusing such risk not only by directly intervening with the person of concern but by also considering external factors influencing the behavior and mental state of the person of concern.

A pre-incident investigation component 446 may be included by the threat assessment assistance module 400 to facilitate pursuit of a meaningful investigation into indicators highlighted through operation of the other components of the threat assessment assistance module 400 and perform the appropriate proactive steps. The pre-incident investigation component 446 may assist with data collection and immediate risk reducing interventions that advantageously assist with mitigating the general risk of violent behavior that affects large numbers of people or the society at large. By identifying threat assessments in general violence risk assessments and pre-incident investigations, increased mitigation of undesirable traumatic events, and adequate response to such an event should one occur, may be achieved.

A digital workspace component 452 may be provided by the threat assessment assistance module 400 and may operate with the assist component 1012 of the external web applications 1000. For example, the digital workspace component 452 may provide a digital workspace, for example a digital whiteboard, to advantageously facilitate visualization of information shared among users, enhance collaboration, present information, and assist with presentations. Those of skill in the art will appreciated additional visual aids that would be included by the digital workspace component after having the benefit of this disclosure.

The threat assessment assistance module may advantageously facilitate meetings via a meetings component 454 to provide users an opportunity to assess and/or reassess risk and intervention management relating to a threat or potential for a violent or divergent act to occur. For example, as violence and threat risk assessment activities near completion, it may become evident as to what the primary risk enhancers are and therefore who is the logical lead user for the remainder of the case or observation. Many team members present during the early stages of the case may no longer be needed but may be available as an original team (agency) member if needed again. The team does have not abandon the leads, but the goal of successful intervention is that fewer and fewer resources are needed to support the person of concern and/or their families and others as time goes on and the reduction of risk of harm to others and/or self.

In one example, a case that has at least two or more significant risk enhancing variables that requires at least two or more different violence and threat risk assessment partners to remain involved in order to lower the level of risk and obtain lasting gains may be classified as a complex case. Cases that reach this level of intervention planning may place a special emphasize on pre-determined follow-up meetings where related team members come together personally or electronically, for example via the meeting module or via telephone conference, to report and review the current state of the case. Sometimes data may be obtained in these meetings that confirms the interventions are working or that follow through did not occur when the person of concern claimed it did. Time periods for follow-up meetings (for example, thirty-day, ninety-day, one-year, and other periods for follow-ups, without limitation) may substantially assist with management of high-risk cases have assisted tremendously with ensuring a high-risk case does not fall through the cracks.

The machine learning engine will now be discussed in greater detail. The machine learning engine may compare at least part of the data included by the threat assessment assistance database 402 to identify correlations and predict a statistical probability of worrisome behavior. The machine learning engine may be communicatively connected to a database or other data structure and may be addressable via API, including an external API. The machine learning engine may import and/or use external data to train the models operated by the machine learning engine, advantageously benefitting from expanded scope of interpretations, trend identifications, temporal insight, and detection and correlation of other useful information for the internally and externally sourced data.

In one example, the machine learning engine may include self-training aspects. For example, machine learning algorithms may be self-trained in a semi-supervised manner, as will be appreciated by those of skill in the art. The machine learning engine may advantageously identify links, correlations, associations, and other significant data patterns that could indicate a probability of an outcome occurring given a certain parameter and/or variable.

Additionally, the machine learning engine may include communication aspects to facilitate interaction by a user with a system enabled by this disclosure. For example, the machine learning engine may power chat-bots to perform initial consultation with users, to gather information, and to categorize information for appropriate response by professional. An illustrative machine learning engine may additionally include a recommendation engine, which may facilitate making a recommendation for a user to follow up on an incident, person of concern, or other condition. The recommendation engine may additionally suggest another course of action based on information provided to the machine learning engine.

The machine learning engine may rank critical periods pertaining to a person of concern. For example, the machine learning engine may categorize a stage or timing relative to a person of concern. The machine learning engine may predict a statistical likelihood of the person of concern acting in a divergent or violent manner. The machine learning engine may categorize the stage of a person of concern using a scale, for example and without limitation, a 1-5 scale. In this illustrative scale, provided without the intent to limit any applicable scale to only 5 levels, a level 1 indication may suggest that an immediate traumatic event is likely to occur. Conversely, in this example, a level 5 indication may suggest that the threat of an immediate traumatic event may be low, but a ripple effect may be likely to occur given detected conditions.

The machine learning engine may advantageously weigh effective properties to improve the predictive accuracy of a statistically likely outcome relating to an incident and/or a person of concern. Weights may be applied based on factors such as time, distance, communication, location, relevance, history, and other factors that would be appreciated by a person of skill and the art after having the benefit of this disclosure.

Persons of concern being categorized via the machine learning engine may be tracked geographically and may be linked to other events and information relating to the person of concern. Reports and information provided by witnesses may be associated with a profile for a person of concern, which may be assisted by the machine learning engine. If multiple persons of concern are being tracked, for example independently, events that link these multiple persons of concern may be reflected as associations in the threat assessment assistance module.

The external web module will now be discussed in greater detail. FIGS. 1-3 and 10 highlight examples of the external web module, which may also be shown in other figures. The external web applications module 1000 may include various components and may include and/or be communicably connected to an external web applications database 1002. The external web applications module 1000 may be operatively connected to the threat assessment assistance module 400, for example, via API connection. Components of the external web application module may include an assist component 1012, training schedule component 1014, self-assessment component 1022, outreach component 1024, and other components that would be apparent to a person of skill in the art after having the benefit of this disclosure.

The external web applications module 1000 may include an assist component 1012, which may facilitate a third party with submitting an incident report or concern with the operators of the threat in the assessment assistance module 400. The assist component 1012 may be provided in a business-to-business context, whereby businesses may quickly and easily provide an incident report that may be followed up by professionals using the threat assessment assistance module 400.

The assist component 1012 may be operatively connected to the threat assessment assistance module 400 via an API connection to share information relating to an externally provided tip which may relate to a person of concern. In one embodiment, the threat assessment assistance module 400 may match the anonymous tip with the profile of a person of concern if available.

The assist component 1012 may be provided using a black box environment, as will be appreciated by those of skill in the art. Information provided through the assist component may be at least partially anonymized. An interface for the assist component may include instructions for an operator on how to provide information. In one example, instructions may include, "if you think this is something of concern, click this button to submit to Assist." In embodiments that provide a black box environment, submitters may be encouraged to provide information they otherwise would withhold due to the promise of anonymity and to relieve the submitter from fears of repercussions for submitting such information.

Information submitted through the assist component 1012 may be parsed for semantic mapping, correlations, metadata, and other information that may facilitate assessment of risk relating to a person of concern for which the submission relates. In some embodiments, general information may be collected along with the submission such as location, internet protocol address, edits, viewers, likes, shares, tags, and other information that would be appreciated by a person of skill in the art after having the benefit of this disclosure.

The external web applications module 1000 may include a training schedule component 1014, which may advantageously assist an external user with managing training activities, which may be associated with activities provided through the threat assessment assistance module 400, the learning portal module 500, the response coordination module 700, and/or other modules of a system enabled by this disclosure. Information received through the training schedule component 1014 may be stored in the external web application database 1002 and may be communicated with various modules of a system enabled by this disclosure via direct and/or indirect communication through the API.

The external web applications module 1000 may include a self-assessment component 1022, which may facilitate monitoring the emotional and physical wellbeing of a person of concern or another user. The self-assessment component 1022 may advantageously facilitate self-assessment of an emotional condition by the user, which can be associated with a profile related to the user. For example, a person of concern may interact with the self-assessment component 1022 to generate and/or access information relating to their own potential for violent and/or divergent tendencies.

An illustrative self-assessment component 1022 may include a questionnaire, a graphical interface, and/or another interactive feature to promote self-reporting of emotional and physical well-being. For example, a brief questionnaire may prompt a user to provide information regarding their current state of well-being. In another example, an array of illustrated faces may be provided to a user ranging from happy to unhappy, which may encourage the user to interact with the faces since minimal effort will be required to perform a self-assessment.

The external web applications module 1000 may include an outreach component 1024, which may provide a channel of communication for submission of the information relating to the person of concern by a third party, the information being includable in the database 402 of the threat assessment assistance module 400. The outreach component 1024 may advantageously provide a channel of communication for submission of the information relating to the person of concern by a third party, the information being includable in the threat assessment assistance database 402 once received by the threat assessment assistance module 400.

The outreach component 1024 may advantageously facilitate referral for professionals and other people to interact with the various modules provided by a system and enabled by this disclosure. The outreach component may advantageously provide authenticated user-based sharing of information and other data. For example, a user of a system enabled by the disclosure may share access to interact with such a system with an unauthenticated user. For example, this unauthenticated user may be given guest access and limited interactivity with such a system enabled by this disclosure. In some embodiments, the unauthenticated user may refer additional unauthenticated users. Additionally, in some embodiments, authentic and/or unauthenticated users may identify and/or refer additional person(s) of concern and information relating to the person(s) of concern.

Information related to and provided by the non-user may be associated with a profile for a user, such as a referring user, and/or person of concern monitored within the system. In one example, a non-user associated via the outreach component 1024 may be identified by a user as an associate of a person of concern. In this example, the associate may be monitored for possible indications of worrisome behavior that may lead to occurrence of a traumatic and/or divergent event by the person of concern or the associate.

In another example, a user may be infected with a highly contagious disease, for example during a viral pandemic, and may identify non-users through the outreach component to facilitate contact tracing. If it is determined that the non-user becomes infected, the non-user may convert to a full user of the system and may add their own non-users through the outreach component for further contact tracing.

The outreach component 1024 advantageously facilitates interaction by witnesses of worrisome behavior. In this example, witnesses may interact with the outreach component 1024 in approximately real-time, in which a person of concern or another identified person may be monitored. By interacting with the outreach component 1024, non-users may assist with gathering and organizing information relating to a perpetrator of a violent act, assessing worrisome behavior of a person of concern, facilitating communication between multiple parties, assisting with building a profile by providing additional information to be considered by a system enabled by this disclosure, for example, the threat assessment assistance module 400, and other information.

Submissions via the outreach component 1024 may be analyzed by the machine learning engine. For example, the machine learning engine may perform photo matching, language pattern recognition, voice sample comparison, writing sample analytics, and other information. In the example of analyzing commonality and writing samples, various factors may be considered such as handwriting, language, grammar, letter structure, and other identifiers that will be appreciated by a person of skill in the art after having the benefit of this disclosure.

Interaction with the outreach component 1024 may be logged and/or recorded for future analysis by professionals, users, the machine learning engine, and/or other parties. Participants of the outreach component 1024 may send information via a module of a system enabled by this disclosure, such as a generalized version of the client portal module 600.

In some embodiments, participants of the outreach component 1024 may be excluded from access to the threat assessment assistance module 400. Information received through the outreach component 1024 may be screened, monitored, categorized, and otherwise processed by users of the threat assessment assistance module 400. Useful and derivative information may be generated via the threat assessment assistance module 400 using the reported information gathered through the outreach component 1024.

The learning portal module will now be discussed in greater detail. FIGS. 1-3 and 5 highlight examples of the learning portal module, which may also be shown in other figures. The learning portal module 500 may advantageously facilitate sharing of training materials and other information to assist in the detection of threats, detection of risk for a violent event to occur, training on trauma response, participation in and operation of the features provided by the response coordination module, and provide assistance to troubled individuals to help mitigate the likelihood of them committing a violent or divergent act. The learning portal module 500 may provide training materials and information to not only school administrators or law enforcement, but to other groups such as teachers, parents, patrol men and women, and others. The learning portal may additionally provide educational and/or instructional content regarding work environments, toxicity of social environments, training programs, trauma management, crisis response management, sensitivity training, and other topics consistent with the scope and spirit of this disclosure.

The learning portal module 500 may require users to login prior to receiving access to the features of this module. A login screen may be displayed to the user through a connected module, such as the client portal module 600 and/or the mobile application module 920. The login of a user may control permissions available to the user to access other content that may be provided by a system enabled by this disclosure.

The learning portal module 500 may provide a dashboard interface to authorized users to display information relating to operation of a system enabled by this disclosure, such as for quickly viewing learning portal content or accessing credentials and badges from completed content. A dashboard screen may be displayed to the user through a connected module, such as the client portal module 600 and/or the mobile application module 920.

The learning portal module 500 may advantageously assist educating professionals and other users of the platform to detect persons of concern and recognize behavioral patterns that may indicate the risk of a future violent or divergent event. Users may train using the learning portal module 500, which may include various materials and curricula accessible via a database operatively connected to the learning portal module. Various components may be included by the learning portal module to facilitate the distribution of content, learning materials, certifications, and metrics regarding achievements in the learning portal without limitation.

The learning portal module 500 may include permission management, which may affect sharing of information with the client portal module 600 and/or other modules that may be operatively connected to the learning portal module 500 of a platform enabled by this disclosure. The components of the learning portal module 500 may include data, which may be stored and made accessible by a learning portal database 502 operatively connected to the learning portal module, for example, via network communication interface.

The training portal module 500 may include a learning portal database 502, in which electronic instructions relating to the components of the learning portal module 500 may be stored and/or read to be executed by a computerized device having a processor and memory. The learning portal module may include various components, such as an operative connection to a user profiles component managed by a client portal module 600, content component 512, e-commerce component 514, certificates and accreditation component 522, training schedule classes component 524, quizzes and tests component 532, and participation component 534, without limitation. Those having skill in the art will appreciate that additional components may be included and/or some of the above-mentioned components may be excluded without limitation after having the benefit of this disclosure.

The learning portal module 500 may access and/or include information about the professional or other user of the learning portal module 500 via a user profiles component of a client portal module 600, which will be discussed in greater detail below. Information provided relating to a user profile may advantageously be used to track a user's progress and assist with suggesting training materials best suited for the role and needs of the user.

A content component 512 may also be included by the learning portal module 500 to distribute materials to be viewed and consumed by users identified by the user profiles accessible via the client portal module 600. Users may access the information provided via the content module via a connected module, such as the client portal module 600 and/or the mobile application module 920. Content may include written content, video content, audio content, interactive instruction, and other materials that may assist with the education and training of users of the learning portal module 500, without limitation.

Content may be designated as being free, included by a subscription, included by a license, available for purchase, or otherwise marketable to users of the learning portal module. Content may be provided as an on-demand stream, consumed at the convenience of a user, provided in a classroom setting, provided in a seminar setting, or otherwise provided in a manner that would be appreciated by a person of skill in the art. In some embodiments, content may be provided in a form of instruction adherent to a schedule. Examples of scheduled instruction may include recurrent classes, seminar events, training sessions, online classes, and/or hybrid learning structures that may mix on demand portions with scheduled portions of instruction and content. Content may also be made accessible and/or deliverable according to the level of a user.

Illustrative content may be related to a foundations certificate program and may include foundational training and materials relating to threat assessment, trauma response, family dynamics, and other related topics. For example, threat assessment content may include instruction regarding an evolutionary process for understanding violence and introduce the consumer to the early research, concepts and variables that led to the development of the comprehensive threat assessment models, such as the NACTATR™ Violence Threat Risk Assessment (VTRA™) model—the only known community-based multidisciplinary model developed to address substantially all forms of violence simultaneously by considering multiple forms of violence including, family, community, school and workplace.

In another example, trauma response content may include instruction regarding understanding trauma, for example via the NACTATR Traumatic Event Systems (TEST™) model of crisis and trauma response, to consider unique characteristics of the individuals, families, schools, workplaces, or communities being supported. In this example content may be used to train a user to avoid assuming that every human being or human system functions the same, therefore trauma response should be measured to the actual circumstance of those being supported.

In an additional example, family dynamics content may include instruction regarding presentation of issues unique to each individual entering counselling, with consideration of other typical factors that can elevate risk for symptom development that are "outside" the individual. In other words, family dynamics content may provide instruction that teaches counseling techniques that are not all about the identified person, but also considers family dynamics as a risk enhancing variable that can contribute to what may be wrong with an individual as well. Through this illustrative family dynamics content, understanding of family dynamics can be considered a solution to many problems by expanding knowledge on key insights that have influenced clinical practice throughout the world and elements from the fields of threat assessment and trauma response that are sometimes family-generated.

An e-commerce component 514 may be included by the learning portal module 500 to facilitate commercial transactions relating to the purchase, licensing, or otherwise granted permission to access content provided through the learning portal module 500. The e-commerce component 514 may assist with purchasing of content or a license to view and use content provided by the content component 512. The e-commerce component 514 may assist with payment processing, content selection, online storefronts, and other market aspects that would be appreciated by a person of skill in the art after having the benefit of this disclosure.

Additionally, the e-commerce component 514 may manage licenses, accept payments, or otherwise process the transfer of funds between a user desiring to consume materials through the learning portal module 500 and the delivery of such materials through the learning portal module 500. In one embodiment, the e-commerce component 514 may additionally manage shared distribution of revenue between content providers and the consumption platform.

A certificates and accreditation component 522, otherwise referred to as a certifications badges and transcripts component without limitation, and participation component 534 may be provided to disburse and manage credentials of a user. As users specified by a communicably connected user profile component engage with the content included by the content component 512, the users may assess their progress through learning and training by engaging in quizzes and tests provided through the quizzes and test component 532. Users may access the information shown in these illustrative screens through another module, such as the client portal module 600 and/or the mobile application module 920. These quizzes and tests may assess proficiency with the information and other content taught through the learning portal module 500.

The participation component 534, otherwise referred to as an enrollment attendance and grading component without limitation, may be included by the learning portal module 500 to analyze performance of a user. Results of the quizzes and tests and other metrics relating to interaction with the learning portal module 500 may be managed and graded by the participation component 534. Users receiving satisfactory marks and proficiency in the content consumed may be given certificates, badges, transcripts, or other indications of successful completion via the certificates and accreditation component 522 for satisfactory understanding of the content provided through the learning portal module 500. These certifications, badges, transcripts, and other indications of proficiency may be included by and managed through a certificates and accreditation component 522. Levels of proficiency may be determined considering factors such as professional experience, education, interaction with gamification features, prior involvement with responses to violent and/or divergent events, certifications, and other factors that will be apparent to a person of skill in the art after having the benefit of this disclosure.

A training schedule classes component 524 may be provided to assist a user with managing a schedule related to classes and content to be consumed through the learning portal module 500. Users may schedule content for live webinars, in-person classes, on-demand content, timed-access content, and other content to be consumed by a user. If access to desired content expires, a user may request additional access via the training schedule classes component 524.

A quizzes and test component 532 may be provided to assess proficiency in an area of knowledge for a user. Proficiency may be linked to content consumed through the learning portal module 500, such as educational content and training materials. Quizzes may be administered through the quizzes and test component 532, upon successful completion of which may result in issuance of certifications, badges, and/or transcripts via the certificates and accreditation component 522. Metrics relating to performance indicated by the quizzes and test component 532 may be additionally managed via the participation component 534 of the learning portal module 500, without limitation.

In some embodiments, the learning portal module 500 may be white labeled to include branding of an organization hosting training events. In this example, information collected through operation of a white labeled version may still be used to improve the system and to assist with improvements to this and/or other modules.

In at least one embodiment, the learning portal module 500 may be operatively connected to the threat assessment assistance module 400 to provide information from the threat assessment assistance module 400 within the context of content delivered through the learning portal module 500. In this example, without limitation, information associated with the threat assessment assistance module 400 may be provided to the learning portal module 500 via one or more API connections. In an example where the learning portal module 500 and the threat assessment assistance module 400 are not directly connected through an API, data may be shared between such modules through an intermediary module such as the messaging module 900 and/or the client portal module 600.

The training evaluation module will now be discussed in greater detail. FIGS. 1-3 highlight examples of the training evaluation module, which may be shown in other figures. The training evaluation module 940 may advantageously gather and share feedback relating to content and other materials provided to users for training, such as consumed through the learning portal module 500. The training evaluation module 940 may include user profiles indicative of users submitting and evaluation and/or users participating in learning portal content consumption and/or attendance to training events.

The training evaluation module 940 may additionally include surveys to assess the effectiveness of training materials, event coordination, and to provide feedback on how content is delivered, consumed, retained, and applied. Once a user has completed a survey, the results may be captured using the survey capture feature. Information captured through surveys may be included in a database operatively connected to the training evaluation module 940. This information may be aggregated, anonymized, analyzed, and/or used to improve the techniques and content being provided to users through the learning portal module and/or other training events.

The client portal module will now be discussed in greater detail. FIGS. 1-3 and 6 highlight examples of the client portal module, which may also be shown in other figures. The client portal module 600 may additionally be referred to as a client platform module or NCP module, without limitation. The client portal module 600 may advantageously provide a user with a common graphical user interface (GUI) displayable to the user. By including a client portal module 600, a platform enabled by this disclosure may advantageously eliminate the need for multiple disparate applications that would otherwise require unwieldy use by professionals.

The client portal module 600 may advantageously provide a more streamlined and integrated platform for accessing and managing information relating to risk of future violent events, handling of existing violent events, and learning about how to prevent future events through studies of existing knowledge relating to such events. Features may be included by the client portal module 600 to encourage continued use by professionals and other users such as gamification, rewards, and other features that will be appreciated by skilled artisans.

The client portal module 600 may advantageously provide a social platform for interaction among users, content sharing, networking, electronic publication of information and credentials, directory of users, and other useful features to facilitate collaboration and sharing of information between users of a system enabled by this disclosure. Users of the client portal module 600 may access information held by modules connected to the client portal module 600, for example, as included by a system enabled by this disclosure and communicably connected via API, such as over a network.

The client portal module 600 may be provided as a central hub for users of a platform enabled by this disclosure. Users may access the client portal module 600 upon logging in to a system that includes other modules. These users may access the information included by additional modules of such a platform through interaction with the client portal module 600.

For example, a user may log into modules of a system enabled by this disclosure via the client portal module 600. The user may access threat assessment tools provided via the threat assessment assistance module 400 by engaging with the interface provided by the client portal module 600. Information from the threat assessment assistance module 400 may be shared with the user via a telecommunications connection between the threat assessment assistance module 400 and the client portal module 600. In another example, information and content provided through the learning portal module 500 may be shared with and consumed by a user via an interface provided through the client portal module 600. Credentials earned through the learning portal module 500 may be posted to a profile hosted by the client portal module 600 and optionally made viewable by other users accessing the client portal module 600. Access to various features across a system enabled by this disclosure may be controlled, presented, managed, and otherwise affected by the client portal module 600, without limitation.

The client portal module 600 may include a user profiles component 612, training transcript badges and certificates component 614, permissions component 622, available trainings component 624, custodial data and permissions key component 632, usage and metrics component 634, and team invites component 642, without limitation.

A user profiles component 612 may be included by the client portal module 600 to assist with collecting and managing information relating to a user. For example, a user may define their username, password, subscription level, access, associations, and other data relating to their usage of a system such as enabled by this disclosure. Details relating to a user profile may be managed and updated using the user profiles component 612 of the client portal module 600. Metrics relating to performance by a user in other modules may also be reflected in a user profile managed through the user profile component 612.

A training transcripts badges and certificates component 614 may be included by the client portal module 600 to manage certificates transcripts and badges relating to training events and other interaction with the various modules of a system enabled by this disclosure. Badges may relate to awards given through gamification, completion of content through the learning portal module 500, interaction through the threat assessment assistance module 400, and deployment and interaction via the response coordination module 700, without limitation. Users may view transcripts, badges, certificates, and other metrics via the training transcripts component 614. In one embodiment, badges, certificates, rewards, credentials, qualifications, and other indicators of a capacity of a user may be shared with other users via the client portal module 600. Sharing of accomplishments and credentials may be posted to a newsfeed that may distribute information to other users, listed in a user's profile, or otherwise shared with other users as would be appreciated by a person of skill in the art after having the benefit of this disclosure. Access to shared content may be controlled and/or filtered by definable metrics, such as degrees of connection, shared connections, shared networks, or other indications that a consumer of the posted content is authorized to access such content.

In one embodiment, the client portal module 600 may include a permissions component 622 to manage permissions associated with a user to engage with other modules of the platform enabled by this disclosure. For example, permissions managed by a client portal module 600 may control access to additional modules, access to limited feature sets of additional modules, availability of data provided through additional modules, access to APIs used to exchange data between the modules, and other access characteristics that would be appreciated by a person of skill in the art. These permissions may be associated with custodial data and permission keys, which may be managed and/or controlled via the custodial data and permissions keys component.

Permissions may be updated, such as if the role of a user changes through continued use with the platform or with accumulation of transcripts, badges, or certificates through the learning portal module. In one embodiment, permissions may be incrementally added as a person progresses through gamification as a reward for accomplishing criteria of tasks and training objectives.

An available trainings component 624 may be provided through the client portal module 600 to facilitate sharing of information relating to upcoming training sessions, educational content, and other interactions available to a user based on their participation, credentials, and other metrics that may deem a user qualified to access a feature or content. The available trainings component 624 may interact with other components, which may span other modules, for example scheduling components of the various modules.

A custodial data permissions keys component 632 may be provided by the client portal module 600 to assist with the management of permissions relating to sharing of information and access of the other modules of a system enabled by this disclosure. Custodial data may be stored in databases related to the corresponding modules, with access to such data being managed through permissions controlled through a managing module, such as the client portal module 600 in this example. Permission keys may be managed through the managing module, which in this example is the client portal module 600, with access and control being affected accordingly.

A usage and metrics component 634 may be included to assist with gathering and maintaining metrics relating to use of other modules. For example, metrics may be gathered for usage of the threat assessment assistance module 400, consumption of content via the learning portal module 500, access to interactive components such as messaging and/or communication with teams and groups, invites, and other aspects that will be appreciated by those of skill in the art after having the benefit of this disclosure. In one example, usage and metrics may be analyzed to determine popularity, usefulness, and benefits of a features for a desired type of response by a user. Features may benefit for targeted development and improvement based on the usages and metrics received from user interaction with the client portal module 600 and other modules of a system enabled by this disclosure.

A team and invites component 642 may be provided via the client portal module 600 to facilitate building teams of professionals and other users to interact with the other modules of a system enabled by this disclosure. For example, a user may interact with the client portal module 600 to define other users that they work well with or share complementary skill sets to better make use of the features provided through the other modules of this disclosure. The team and invites component 642 of the client portal module 600 may additionally provide users with invitations to participate in educational content provided through the learning portal module 500, response to traumatic events through the response coordination module 700, or assist with the assessment of threats and other traumatic events via the threat assessment assistance module 400, without limitation.

Various components included by the client portal module 600 may benefit from gamification. Inclusion of gamification aspects may advantageously increase engagement with the client portal module 600 and other modules of a system enabled by this disclosure by encouraging progress and rankings resulting from engagement with the system.

In one example, a user may engage with training via the learning portal module 500, which may be accessed through the client portal module 600, to receive certificates and badges for completed sessions. The received badges may be used to decorate the profile of a user, publicly share credentials accumulated and achievements made by the user, and to provide eligibility of the user to be selected to help mitigate the fallout of a violent event, should one occur. The training transcripts, badges, and certificates associated with a user may be retrieved through an API connection with another module, such as the learning portal module 500 discussed above. Additional trainings may be indicated to users through the client portal module 600 of content available through the learning portal module 500 that has not yet been consumed or has recently been added. Received badges, certificates, and other credentials may additionally be posted to a newsfeed that may distribute information to other users. Access may be controlled and/or filtered by definable metrics, such as degrees of connection, shared connections, shared networks, or other indications that a consumer of the posted content is authorized to access such content.

Information relating to the threat assessment assistance module 400 may be shared with a user through the client portal module 600, such as historical activity, highlighted persons of concern, shortcuts to record information relating to a person of concern, worrisome behavior, or incidents. Other information relevant to interaction with the threat assessment assistance module 400 may also be presented to a user for quick access to frequently used content on an individual and/or platform-wide scale.

In one embodiment, communications may be facilitated through use of the client portal module 600. The graphical user interface provided by the client portal module 600 may be structured such to provide a social network environment, such as for a professional social network. The client portal module 600 may work in cooperation with the messaging module 900 to provide messaging between users, for example person to person messaging.

Through use of the client portal module 600, users may access features and functionalities provided by other modules. Examples of these functionalities include access to broker transactions relating to educational content and admission to consume the same, purchase and sale of training materials, storefronts to engage in commerce relating to educational materials and other content purchasable through a platform enabled by this disclosure, and other features that would be apparent to a person of skill in the art after having the benefit of this disclosure. Access to some of the materials provided through the client portal module 600 may be gated based on credentials, time, proficiency, experience, and other metrics that may be determined by an operator of a system enabled by this disclosure.

In one embodiment, a presenter component may be included by the client portal module 600 to facilitate trainers and other users to present materials to be consumed by other users, for example, via the learning portal module 500. Information shared through the presenter component may be designated as time-limited or otherwise access limited.

In one embodiment, aspects of the client portal module 600 may be accessible via the mobile application module 920. For example, the graphical user interface of the client portal module 600 may be adapted for or substantially reproduced via the mobile application module 920. In another example, the graphical interface of the client portal module 600 may be streamed to at least part of the mobile application module 920. In another embodiment, the mobile application module 920 may be an extension of the client portal module 600, without limitation. The client portal module 600 may be formatted to correspond with different computerized devices on which it may be operated, for example, desktop computer, laptop computer, mobile phone, smartphone, iPhone, Android phone, tablet, and/or other devices without limitation.

The response coordination module will now be discussed in greater detail. FIGS. 1-3 and 7 highlight examples of the response coordination module, which may also be shown in other figures. The response coordination module 700 may assist with management and selection of teams designated to respond to violent events, trauma, public health crises, and/or otherwise divergent events. The response coordination module 700 may assist with managing the logistics of distributing resources for such teams to assist with diffusing a violent and/or traumatic event and helping a community heal from such an event.

The response coordination module 700 may include various components to assist with the management and distribution of assets for responders to a violent, crisis, or trauma related event. The response coordination module 700 may include a request for support component 712, a scheduling component 714, a view resources component 722, a stipend management component 724, an information management component 732, and an efficacy component 734, without limitation. Those having skill in the art will appreciate that additional components may be included within the response coordination module 700 after having the benefit of this disclosure. The various components of the response coordination module 700 may be communicably connected to a response coordination database 702. Additionally, the response coordination module 700 and the response coordination database 702 may be communicably connected to exterior modules and/or databases via API.

The response coordination module 700 may be operatively connected to the client portal module 600 and a user profiles included by the client portal module, which may access and retrieve information from other modules included by a platform enabled by this disclosure indicative of profiles of those to be included in the response. The user profile provided by the client portal module may be communicably connected to additional modules providing information regarding user profiles. Information may be exchanged between the various modules and user profiles associated with same via API connections, given appropriate permissions are granted to view such information.

The response coordination module 700 may additionally include a request for support component 712 providing features to request support for the operations being engaged by the user of the response coordination module 700. For example, a responder may request the assistance of investigatory equipment, access to records relating to an event, access to records included by the threat assessment assistance module 400, or other information or materials that may assist with understanding facts surrounding an event and make mitigating the after effects created from such an event more manageable. In an example in which informational materials are requested through the request for support component 712 of the response coordination module 700, those materials may be viewed through a view resources component 722 and/or an interface provided via the client portal module 600.

The response coordination module 700 may additionally include a scheduling component 714 to assist with scheduling shifts, coordinating when each user of the response coordination module 700 will interact with other users, and to assist with locating users and other resources to deployments in which their skills will be most helpful. The scheduling component 714 of the response coordination module 700 may work cooperatively with additional scheduling features of a system enabled by this disclosure, for example a scheduling component associated with the client portal module 600, via API.

The response coordination module 700 may additionally include a resources component 722 to provide resources requested through other components or made available for responders to assist with the response coordination. Resources viewable through the resources component 722 may include documents, audiovisual materials, feedback from other professionals and responders, and other information that would be helpful in the response to a traumatic, divergent, health crisis, and/or violent event.

In one embodiment, information requested through the request for support component 712 may be viewable via the resources component 722. In an additional embodiment, resources viewable through the view resources component 722 may be at least partially sourced from the threat assessment assistance module 400, learning portal module 500, client portal module 600, messaging module 900, and/or other modules, without limitation.

In one embodiment, a stipend management component 724, otherwise referred to as an e-commerce stipend component without limitation, may be included by the response coordination module 700 to assist with managing the allocation of financial resources between professionals and other users and responders interacting through a response coordination module 700, such as one described throughout these examples. The stipend management component 724 may assist with allocating a persistent budget stipend to the responders as agreed upon prior to the responders and other professionals becoming involved with responding to a violent, divergent, traumatic, health crisis, and/or other event. The stipend may be provided by deposit into a bank account, provisioning of a rolling credit, a pay card, or other technique for distributing assets that would be appreciated by those of skill in the art. In the example of a pay card, additional controls may be placed on the stipend and its use, such as acceptable vendors, time-controlled purchases, duration control, and other financial controls.

The stipend management component 724 may additionally manage requests for increased stipends, overtime, procurement of additional resources, and/or other financial necessities not originally contemplated at the outset of deployment for the professionals or users. Funds may be provided for disbursement through the e-commerce stipend component from sponsors, governments, private entities, public funds, or other sources that committed to contribute to managing how to deal with the occurrence of a violent and/or divergent event.

Documents may be stored by the response coordination module 700, for example in a response coordination database 702, via an information management component 732, otherwise referred to as a document management component without limitation. For the purpose of this disclosure, databases in which documents may be stored is intended to be interpreted broadly and may include buckets, such as S3 buckets, as discussed previously in this disclosure. Documents and other information may be retrieved from other modules, such as the threat assessment assistant module 400, given that the requesting user has appropriate permissions to access such information.

The response coordination module 700 may include a local information management component 732 to locally store documents relevant to the response. This local storage of documents may advantageously reduce the number of API calls required to access information from other modules and potentially increase the speed at which such materials can be accessed since they will be retrieved from a local or more direct data path as opposed to being repeatedly retrieved through an API call over an extended network. Locally stored documents and other data may be scheduled for timed deletion, which may occur substantially automatically by the local information management component 732, for example. Device permissions may be requested and/or granted to allow timed deletion on various modules and/or computerized devices operated by a user. For example, a user can agree to allow modification of locally stored files that may enable the deletion of files after a license, session, or lease of content expires or otherwise becomes outdated.

The response coordination module 700 may additionally include an efficacy component 734 to assist with evaluating the responsiveness, effectiveness, and value provided by a responder and/or resources provided to a responder when deployed for response to a traumatic, violent, or otherwise divergent event. Participants that can provide information via the efficacy component 734 may include other responders, victims, persons of concern, users, observers, and/or others related to a response event. Additionally, efficacy of training and learning modules may be determined via the efficacy component 734, without limitation. For example, features provided by the efficacy component 734 may be operatively connected to other modules and components that may provide training to users to collect and derive metrics based on the efficacy of the trainings and practical applicability of the training to the threat assessment, response, and other activities that may be performed by the user.

The efficacy component 734 may provide evaluations to participants, through which the participants may evaluate responders encountered during the response event. Participants may provide reviews relating to other responders, which may include star ratings, written feedback, or other metrics that would be appreciated by a person of skill in the art after having the benefit of this disclosure. Possible information provided during reviews or evaluations may include suggestions for how a responder, or resources provided for a responder, may be improved. By allowing a mechanism for peer review via the efficacy component 734, selection of the best responders given for particular response situations may be improved.

The efficacy component 734 may additionally include information regarding qualifications of a responder to participate in a response event. These qualifications may consider certificates, badges, awards, evaluations, and other information that may be provided through interaction with other modules, for example via API. In one embodiment, qualifications may require recertification, encouraging or requiring continuing education to remain eligible for selection to respond to future violent, traumatic, health crisis, or other divergent events. Information regarding the efficacy of a responder may also be determined by monitoring and/or evaluating interaction with the threat assessment assistance module 400.

The efficacy component 734 may further include information regarding language history. Demographic information may be included relating to language use and history. Vocabulary and terms of art may also be evaluated to determine whether users are learning and retaining vocabulary and other language relating to threat assessment, events, response activities, and other engagements that would relate to using a system enabled by this disclosure. This aspect of the efficacy component may be improved as experience in dealing with a type of event provides new information and tools to address later occurrences and activities of the event or similar events.

In one example, information may be provided by the learning portal module 500 indicative of training sessions and/or educational materials consumed and completed by a potential responder. In another example, a "secret shopper" may be deployed to a response event to monitor and audit one or more responders deployed to a response event.

The training broker module will now be discussed in greater detail. FIGS. 1-3 and 8 highlight examples of the training broker module, which may also be shown in other figures. The training broker module 800 may advantageously assist with distributing seats or licenses to engage in training and other preparatory events. For some training sessions, events may be provided with more seats to such events being sold than can be filled by the sponsor of the event. These seats may then be sold or licensed out to other individuals for a fee, complimentary, or otherwise. Distributing otherwise unused seats may advantageously increase the skill sets of users and their ability to respond should a violent event occur.

The training broker module 800 may include various components, for example a client host component 812, a training seats component 814, a user profiles component 822, a disbursement component 824, an approvals component 832, and an e-commerce collection component 834, without limitation. The various components may operate via electronic instructions stored on a connected training broker database 802. The various components may additionally speak with other modules of a system enabled by the disclosure via API.

The training broker module 800 may include a client host component 812 to include information about the sponsor of an event or training. The training program may additionally include a user profiles component 822 to include information about the users attending the training event or viewing the training materials. Information included by the user profiles component 822 of the training broker module 800 may be at least partially retrieved from other modules such as the client portal module 600. This retrieval of information may be controlled by permissions and may occur via an API.

Request to attend a training or preparatory event or to consume educational content or training content under the license of a host may require approval. For example, a user may request to attend a training event being sponsored by a host should seats become available. The host may then approve the requesting party to attend, with such approval being managed and/or recorded by the approvals component 832 of the training broker module 800. This information may be made accessible by other modules of a platform enabled by this disclosure to ensure access is given to the requesting party that is approved by the event managers. For example, approved guests may be validated by the approvals component 832 of the training broker module 800 when the guest attempts to access information through the learning portal module 500 asserting association with the host. The approvals component 832 may manage assignments of user rights by a host of the events and the educational content.

In some cases, whether a requesting guest user may qualify to attend a training program, their likelihood of acceptance may be relative to the number of seats available for the training event or for access to distributable content via the learning portal module. The number of seats allocated for attendance to a training event may be tracked and managed via a training seats component 814 of the training broker module 800, with available seats being eligible for licensure or sale to guest users. The training seats component 814 may manage an assignment of user rights to participate in events and access the educational content, for example, as hosted by the learning portal module 500. A waitlist may be provided for high-demand events booked to capacity.

The training broker module may advantageously include an e-commerce component to assist with managing the economic aspects of a training event and/or access to learning portal content. The e-commerce component may include subsidiary components, such as the disbursement e-commerce component 824 and collection e-commerce component 834, without limitation. For example, an event coordinator such as a host may receive a disbursement relative to the number of attendees expected to receive such training via a disbursement e-commerce component 824. However, such seats may be resold if attendees are unable to attend such training event or for example the minimum number of seats for a venue exceeds the number of expected attendees. Guest attendees approved to attend on the host behalf, for example via the approvals component 832, may purchase their guest admission to the event. The purchase of resold seats and exchange of related funds may be assisted by the collections e-commerce component 834. For example, the collections e-commerce component 834 may assist with collecting payment for access to the training event prior to registering the guest attendee.

The messaging module will now be discussed in greater detail. FIGS. 1-3 and 9 highlight examples of the messaging module, which may also be shown in other figures. The messaging module 900 may advantageously include tagging functionality that may assist with associating conversations with topics of interest. Commenting, chatting and collaboration features, digital workspaces, notifications, and alerts may be provided or facilitated by the messaging module 900. Chatting and collaboration features may include text chats, document sharing, and/or audiovisual communication. A digital workspace may include tools for sharing documents, digital whiteboards, collaborative construction of documents, information organization and management, and sharing of useful information.

The messaging module 900 may facilitate communication between users of a platform enabled by this disclosure. The messaging module 900 may include interfaces with additional modules of such a platform, for example via exchange of data through an API. Permissions for these additional modules to use aspects of the messaging module 900 and/or communicate information via the messaging module 900 may be controlled through permissions. These permissions may be set by a connected module, such as the client portal module 600.

The messaging module 900 may facilitate communication between groups of varying size. For example, the messaging module 900 may provide direct messaging between a small set of users, for example, two users. Private messaging features may also be provided. The messaging module 900 may also provide group messaging, for example, for groups assigned to respond to a traumatic event via the response coordination module 700. Subsets of a group may be defined as breakout groups, which may provide more targeted communication between members assigned to a more defined tasks in the larger structure of a response event. Breakout meetings may also be established, allowing a definable set of users to communicate regarding a common topic in a meeting-style setting.

In one embodiment, the messaging module may be operatively connected to other modules such to exchange data with the threat assessment assistance module 400, the learning portal module 500, the response coordination module 700, the training broker module 800, and a mobile application module 920, without limitation. Aspects of the messaging module 900 may be integrated into other modules, such as being provided through an interface controlled through the client portal module 600. However, even in instances where the messaging module 900 is accessible and integrated into another module, it may still be provided access to information contained by other modules and databases connected to those modules, such as via API pathways.

In one embodiment, the messaging module 900 may manage the communication structure of a platform enabled by this disclosure. In this embodiment, the messaging module 900 may provide communication among the users of the modules. The communication structure may provide a direct communication pathway between the modules that are directly connected via the API, such by using the messaging module 900 as an intermediary for communications via multiple API pathways. For example, the communication structure may provide a bridged communication pathway between the modules that are indirectly connected via the API by sharing at least one intermediary module being communicably connected to the modules via the API. The intermediary module may relay the communication received by a first connected module via a first API pathway to a second connected module via a second API pathway.

In one embodiment, the messaging module 900 may include communication features that may be used in association with the messaging module 900 and other modules associated with the messaging module 900, without limitation. Communication features may include instant messaging, chatbots, preliminary assessments, a recommendation engine, community communications, directions, private tunnels for encrypted communications, and other communication features that would be appreciated by a person of skill in the art after having the benefit of this disclosure.

In an example including instant messaging features, a live chat client may be provided to users of the various modules facilitating substantially live conversations regarding tactical deployment to a response event, monitoring or observing worrisome behavior from a person of concern or others, attendance or brokerage relating to learning events through the learning portal module 500, and other interactions that may benefit from substantially live communication between various users of a platform enabled by this disclosure.

The messaging module may additionally facilitate communication between users of a platform enabled by this disclosure and persons of concern or others being monitored or otherwise tracked via the platform. For example, professionals with access to the threat assessment assistance module 400 may communicate with a person of concern to monitor their mental well-being, to determine whether the person of concern has a psychological and/or medical condition affecting their behavior, or other communications that may facilitate professionals and other users to monitor a person of concern or others.

The messaging module 900 may facilitate initiating a prioritized communication pathway to administrators or decision makers associated with a system enabled by this disclosure. For example, users of the threat assessment assistance module 400 may collaborate with each other via the messaging module 900 to a threshold where the professionals determine worrisome behavior associated with the person of concern that requires escalation. An instant messaging, chat, or other form of communication session may be initiated with the headquarters of an operator of a system enabled by this disclosure. The administrators may then determine whether intervention, continued monitoring, or preparation for a response to a traumatic event is necessary.

The messaging module 900 may additionally include communication features that may leverage machine learning operations, such as may be provided by the machine learning engine, without limitation. These features may include a chatbot capable of parsing responses provided by a communication participant to perform a preliminary assessment and identification of statistically probable issues. For example, such an assessment may consider whether a person of concern or other matches a defined number of conditions defined in the DSM for potential assessment of a psychological disorder, or other psychological or mental condition that may affect worrisome behavior shown or potentially associated with a person of concern.

In one embodiment, the messaging module 900 may include an encrypted pathway for secured communication between various professionals, agencies, or other users where sensitivity of information is desired to be maintained. In this embodiment, a private tunnel may be created through which communication data may be transmitted from one user to another. Private tunnels may additionally be created for communication between users and administrators, such as at the headquarters of an operation managing a system enabled by this disclosure. Encryption may be provided, for example end-to-end encryption. Other security features may additionally be included to increase security of communication, as will be appreciated by those of skill in the art after having the benefit of this disclosure.

The mobile application module will now be discussed in greater detail. FIGS. 1-3 and 9 highlight examples of the mobile application module, which may also be shown in other figures. The mobile application module 920 may advantageously provide access to the client portal module 600 via a portable electronic device and notifications and alerts relating to the user.

The mobile application module 920 may provide an interface for users to engage with other modules of a platform enabled by this disclosure through a portable electronic device. Users may engage the mobile application module to communicate with one another, access information contained by other modules and respective connected databases, and/or manage the user's role and interaction with the functionality provided through the other modules of the platform.

In one example, the mobile application module 920 may include notifications. These notifications may alert a user if there is an update to information to which they have permission to access, an event that requires a response, new information relating to a person of concern, and other information that would be helpful in the detection and management of worrisome behaviors, incidents, and other aspects that may increase the risk of a violent or divergent event occurring. Notifications may also inform users of creation, status, and attendance information relating to structured meetings. Notifications may be communicated and/or logged via API.

Notifications may additionally include new content becoming available through the learning portal module 500, available seats being offered through the training broker module 800, new assignments and response invitations being listed through the response coordination module 700, structured meetings, and/or other interactions with a platform enabled by this disclosure. Badges, certificates, credentials, and other achievements through gamification may be displayed through the mobile application module 920. This inclusion of gamification rewards may advantageously encourage users to increase their engagement with the mobile application module 920, and therefore with other modules included by a platform including such features.

Users may additionally receive alerts relating to changes of information and/or other interactions with a platform enabled by this disclosure. The alerts may share similarities with notifications. However, the alerts may include heightened urgency and/or other indications that expedited attention is required or requested. News may be shared with users through the mobile application module relating to persons of concern, violent events, developments and the detection and mitigation of violent behavior, and/or other information that may be retrieved through the news. Information distributed through the news component of the mobile application module 920 may be at least partially retrieved from the threat assessment assistance module and associated databases.

Figure 11:
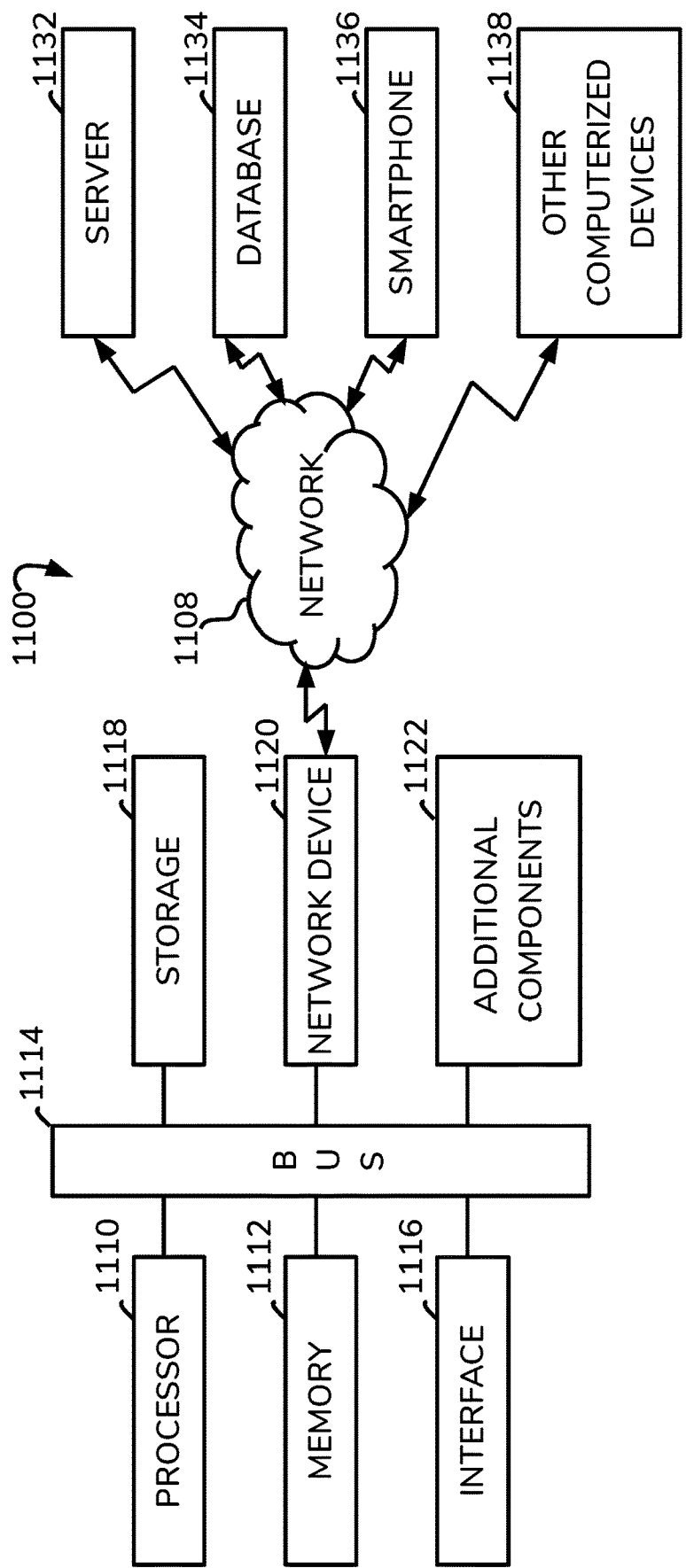
FIG. 11 is a block diagram view of an illustrative computerized device, according to an embodiment of this disclosure.

Referring now to FIG. 11, an illustrative computerized device will be discussed, without limitation. Various aspects and functions described in accord with the present disclosure may be implemented as hardware or software on one or more illustrative computerized devices 1100 or other computerized devices. There are many examples of illustrative computerized devices 1100 currently in use that may be suitable for implementing various aspects of the present disclosure. Some examples include, among others, network appliances, personal computers, workstations, mainframes, networked clients, servers, media servers, application servers, database servers and web servers. Other examples of illustrative computerized devices 1100 may include mobile computing devices, cellular phones, smartphones, tablets, video game devices, personal digital assistants, network equipment, devices involved in commerce such as point of sale equipment and systems, such as handheld scanners, magnetic stripe readers, bar code scanners and their associated illustrative computerized device 1100, among others. Additionally, aspects in accord with the present disclosure may be located on a single illustrative computerized device 1100 or may be distributed among one or more illustrative computerized devices 1100 connected to one or more communication networks.

For example, various aspects and functions may be distributed among one or more illustrative computerized devices 1100 configured to provide a service to one or more client computers, or to perform an overall task as part of a distributed system. Additionally, aspects may be performed on a client-server or multi-tier system that includes components distributed among one or more server systems that perform various functions. Thus, the disclosure is not limited to executing on any particular system or group of systems. Further, aspects may be implemented in software, hardware or firmware, or any combination thereof. Thus, aspects in accord with the present disclosure may be implemented within methods, acts, systems, system elements and components using a variety of hardware and software configurations, and the disclosure is not limited to any particular distributed architecture, network, or communication protocol.

FIG. 11 shows a block diagram of an illustrative computerized device 1100, in which various aspects and functions in accord with the present disclosure may be practiced. The illustrative computerized device 1100 may include one or more illustrative computerized devices 1100. The illustrative computerized devices 1100 included by the illustrative computerized device may be interconnected by, and may exchange data through, a communication network 1108. Data may be communicated via the illustrative computerized device using a wireless and/or wired network connection.

Network 1108 may include any communication network through which illustrative computerized devices 1100 may exchange data. To exchange data via network 1108, systems and/or components of the illustrative computerized device 1100 and the network 1108 may use various methods, protocols and standards including, among others, Ethernet, Wi-Fi, Bluetooth, TCP/IP, UDP, HTTP, FTP, SNMP, SMS, MMS, SS7, JSON, XML, REST, SOAP, RMI, DCOM, and/or Web Services, without limitation. To ensure data transfer is secure, the systems and/or modules of the illustrative computerized device 1100 may transmit data via the network 1108 using a variety of security measures including TSL, SSL, or VPN, among other security techniques. The illustrative computerized device 1100 may include any number of illustrative computerized devices 1100 and/or components, which may be networked using virtually any medium and communication protocol or combination of protocols.

Various aspects and functions in accord with the present disclosure may be implemented as specialized hardware or software executing in one or more illustrative computerized devices 1100, including an illustrative computerized device 1100 shown in FIG. 11. As depicted, the illustrative computerized device 1100 may include a processor 1110, memory 1112, a bus 1114 or other internal communication system, an input/output (I/O) interface 1116, a storage system 1118, and/or a network communication device 1120. Additional devices 1122 may be selectively connected to the computerized device via the bus 1114. Processor 1110, which may include one or more microprocessors or other types of controllers, can perform a series of instructions that result in manipulated data. Processor 1110 may be a commercially available processor such as an ARM, x86, Intel Core, Intel Pentium, Motorola PowerPC, SGI MIPS, Sun UltraSPARC, or Hewlett-Packard PA-RISC processor, but may be any type of processor or controller as many other processors and controllers are available. As shown, processor 1110 may be connected to other system elements, including a memory 1112, by bus 1114.

The illustrative computerized device 1100 may also include a network communication device 1120. The network communication device 1120 may receive data from other components of the computerized device to be communicated with servers 1132, databases 1134, smart phones 1136, and/or other computerized devices 1138 via a network 1108. The communication of data may optionally be performed wirelessly. More specifically, without limitation, the network communication device 1120 may communicate and relay information from one or more components of the illustrative computerized device 1100, or other devices and/or components connected to the computerized device 1100, to additional connected devices 1132, 1134, 1136, and/or 1138. Connected devices are intended to include, without limitation, data servers, additional computerized devices, mobile computing devices, smart phones, tablet computers, and other electronic devices that may communicate digitally with another device. In one example, the illustrative computerized device 1100 may be used as a server to analyze and communicate data between connected devices.

The illustrative computerized device 1100 may communicate with one or more connected devices via a communications network 1108. The computerized device 1100 may communicate over the network 1108 by using its network communication device 1120. More specifically, the network communication device 1120 of the computerized device 1100 may communicate with the network communication devices or network controllers of the connected devices. The network 1108 may be, for example, the internet. As another example, the network 1108 may be a WLAN. However, skilled artisans will appreciate additional networks to be included within the scope of this disclosure, such as intranets, local area networks, wide area networks, peer-to-peer networks, and various other network formats. Additionally, the illustrative computerized device 1100 and/or connected devices 1132, 1134, 1136, and/or 1138 may communicate over the network 1108 via a wired, wireless, or other connection, without limitation.

Memory 1112 may be used for storing programs and/or data during operation of the illustrative computerized device 1100. Thus, memory 1112 may be a relatively high performance, volatile, random access memory such as a dynamic random-access memory (DRAM) or static memory (SRAM). However, memory 1112 may include any device for storing data, such as a disk drive or other non-volatile storage device. Various embodiments in accord with the present disclosure can organize memory 1112 into particularized and, in some cases, unique structures to perform the aspects and functions of this disclosure.

Components of illustrative computerized device 1100 may be coupled by an interconnection element such as bus 1114. Bus 1114 may include one or more physical busses (for example, busses between components that are integrated within a same machine), but may include any communication coupling between system elements including specialized or standard computing bus technologies such as USB, Thunderbolt, SATA, FireWire, IDE, SCSI, PCI and InfiniBand. Thus, bus 1114 may enable communications (for example, data and instructions) to be exchanged between system components of the illustrative computerized device 1100.

The illustrative computerized device 1100 also may include one or more interface devices 1116 such as input devices, output devices and combination input/output devices. Interface devices 1116 may receive input or provide output. More particularly, output devices may render information for external presentation. Input devices may accept information from external sources. Examples of interface devices include, among others, keyboards, bar code scanners, mouse devices, trackballs, magnetic strip readers, microphones, touch screens, printing devices, display screens, speakers, network interface cards, etc. The interface devices 1116 allow the illustrative computerized device 1100 to exchange information and communicate with external entities, such as users and other systems.

Storage system 1118 may include a computer readable and writeable nonvolatile storage medium in which instructions can be stored that define a program to be executed by the processor. Storage system 1118 also may include information that is recorded, on or in, the medium, and this information may be processed by the program. More specifically, the information may be stored in one or more data structures specifically configured to conserve storage space or increase data exchange performance. The instructions may be persistently stored as encoded bits or signals, and the instructions may cause a processor to perform any of the functions described by the encoded bits or signals. The medium may, for example, be optical disk, magnetic disk, or flash memory, among others. In operation, processor 1110 or some other controller may cause data to be read from the nonvolatile recording medium into another memory, such as the memory 1112, that allows for faster access to the information by the processor than does the storage medium included in the storage system 1118. The memory may be located in storage system 1118 or in memory 1112. Processor 1110 may manipulate the data within memory 1112, and then copy the data to the medium associated with the storage system 1118 after processing is completed. A variety of components may manage data movement between the medium and integrated circuit memory element and does not limit the disclosure. Further, the disclosure is not limited to a particular memory system or storage system.

Although the above described illustrative computerized device is shown by way of example as one type of illustrative computerized device upon which various aspects and functions in accord with the present disclosure may be practiced, aspects of the disclosure are not limited to being implemented on the illustrative computerized device 1100 as shown in FIG. 11. Various aspects and functions in accord with the present disclosure may be practiced on one or more computers having components other than that shown in FIG. 11. For instance, the illustrative computerized device 1100 may include specially-programmed, special-purpose hardware, such as for example, an application-specific integrated circuit (ASIC) tailored to perform a particular operation disclosed in this example. While another embodiment may perform essentially the same function using several general-purpose computing devices running Windows, Linux, Unix, Android, iOS, MAC OS X, or other operating systems on the aforementioned processors and/or specialized computing devices running proprietary hardware and operating systems.

The illustrative computerized device 1100 may include an operating system that manages at least a portion of the hardware elements included in illustrative computerized device 1100. A processor or controller, such as processor 1110, may execute an operating system which may be, among others, an operating system, one of the above mentioned operating systems, one of many Linux-based operating system distributions, a UNIX operating system, or another operating system that would be apparent to skilled artisans. Many other operating systems may be used, and embodiments are not limited to any particular operating system.

The processor and operating system may work together to define a computing platform for which application programs in high-level programming languages may be written. These component applications may be executable, intermediate (for example, C# or JAVA bytecode) or interpreted code which communicate over a communication network (for example, the Internet) using a communication protocol (for example, TCP/IP). Similarly, aspects in accord with the present disclosure may be implemented using an object-oriented programming language, such as JAVA, C, C++, C#, Python, PHP, Visual Basic .NET, JavaScript, Perl, Ruby, Delphi/Object Pascal, Visual Basic, Objective-C, Swift, MATLAB, PL/SQL, OpenEdge ABL, R, Fortran or other languages that would be apparent to skilled artisans. Other object-oriented programming languages may also be used. Alternatively, assembly, procedural, scripting, or logical programming languages may be used.

Additionally, various aspects and functions in accord with the present disclosure may be implemented in a non-programmed environment (for example, documents created in HTML5, HTML, XML, CSS, JavaScript, or other format that, when viewed in a window of a browser program, render aspects of a graphical-user interface or perform other functions). Further, various embodiments in accord with the present disclosure may be implemented as programmed or non-programmed elements, or any combination thereof. For example, a web page may be implemented using HTML while a data object called from within the web page may be written in C#. Thus, the disclosure is not limited to a specific programming language and any suitable programming language could also be used.

An illustrative computerized device included within an embodiment may perform functions outside the scope of the disclosure. For instance, aspects of the system may be implemented using an existing commercial product, such as, for example, Database Management Systems such as a SQL Server available from Microsoft of Redmond, Wash., Oracle Database or MySQL from Oracle of Redwood City, Calif., or integration software such as WebSphere middleware from IBM of Armonk, N.Y.

In operation, a method may be provided for facilitating communication relating to threat assessment and response. Those of skill in the art will appreciate that the following methods are provided to illustrate an embodiment of the disclosure and should not be viewed as limiting the disclosure to only those methods or aspects. Skilled artisans will appreciate additional methods within the scope and spirit of the disclosure for performing the operations provided by the examples above after having the benefit of this disclosure. Additional methods apparent after having the benefit of this disclosure are intended to be included by this disclosure.

In one illustrative operation, modules including components and a database may be operated for assessing a threat and facilitating a response. Components of the modules may execute electronic instructions to perform functions beyond the capacity of a human operator not having the benefit of a system enabled by this disclosure. The database may be siloed with the module and communicably connected to the component to store the at least part of the electronic instructions and data associated with the module. Data may communicate between the modules via an application programming interface (API). Data stored by the database may be made directly available to the component of the module. Alternatively, data stored by the database may be made selectively available to the requesting entity via the API as governed by the permissions. As discussed throughout this disclosure, the storage of data is intended to additionally include data stored in databases, memory, buckets, flat files, and other memory storage structures consistent with the scope and spirit of this disclosure.

The operation may include managing permissions via a permissions structure to selectively grant access to exchange data stored by the database of the module. The operator may request execution of electronic instructions of a component included by the module.

The operator may also manage communications via a communication structure. Communications management may include selectively transferring at least some data between the module and the requesting entity as permitted by the permissions structure via the API of the module. Communications management may provide a direct communication pathway between the modules that are directly connected via the API. Alternatively, communications management may provide a bridged communication pathway between the modules that are indirectly connected via the API. The bridged communications pathway may operate by sharing at least one intermediary module being communicably connected to the modules via the API. The intermediary module may relay communication received by a first connected module via a first API pathway to a second connected module via a second API pathway.

In this example, the threat assessment assistance module may be operated for identifying a person of concern and organizing the data relating to the person of concern via a profiles and peoples component. Worrisome behavior may be monitored via a worrisome behavior component. Information relating to the person of concern may be monitored to maintain a record and recommend activity corresponding with the record via an analytics component. Additionally, conditions may be monitored that may affect a risk of harm to the person of concern and others via a risk enhancers component.

In this example, the response coordination module may be operated for organizing responders for deployment to a site of a traumatic event via a scheduling component. The response coordination module may additionally permit requesting resources to support the responders via a resources component and managing information sharing among the responders via an information management component.

In this example, the client portal module may be operated for managing the information associated with a user via a profiles component and displaying a graphical user interface (GUI) to the user. The client portal module may also provide capabilities of comparing at least some data included by the database of the threat assessment assistance module to identify correlations and predict a statistical probability of the worrisome behavior. The comparison may be performed via a machine learning engine. The client portal module may additionally permit selectively communicating among external applications having sufficient permissions with other modules and data associated with those other modules. Communications may be provided among the users of the modules via a messaging module.

In this operation, the threat assessment assistance module may further permit organizing the information relating to familial organization including genealogy and the worrisome behavior associated with a family member of the person of concern via a genogram component. The threat assessment assistance module may also permit analyzing the information provided by the genogram component by the threat assessment assistance module and deriving insight relating to the person of concern from the information. Through the threat assessment assistance module, a third-party data reporting service may communicate data relating to monitored social media network activity of the person of concern via a social media analysis request component. Third-party data reporting services may communicate with the social media analysis request component via the API. The threat assessment assistance module may permit predicting a change in behavior of the person of concern via a domains and beliefs component by assessing a change in domain-focused factors and a change in belief-focused factors.

Additionally, in this illustrative operation, the learning portal may be operated for distributing educational content stored in the database associated with the learning portal module. The learning portal module may permit managing qualifications for participating in the deployment and the access to data associated with the threat assessment assistance module via a certificate and accreditation component. The learning portal module may also permit managing enrollment, attendance, and grading relating to the educational content via a participation component.

Figure 12:
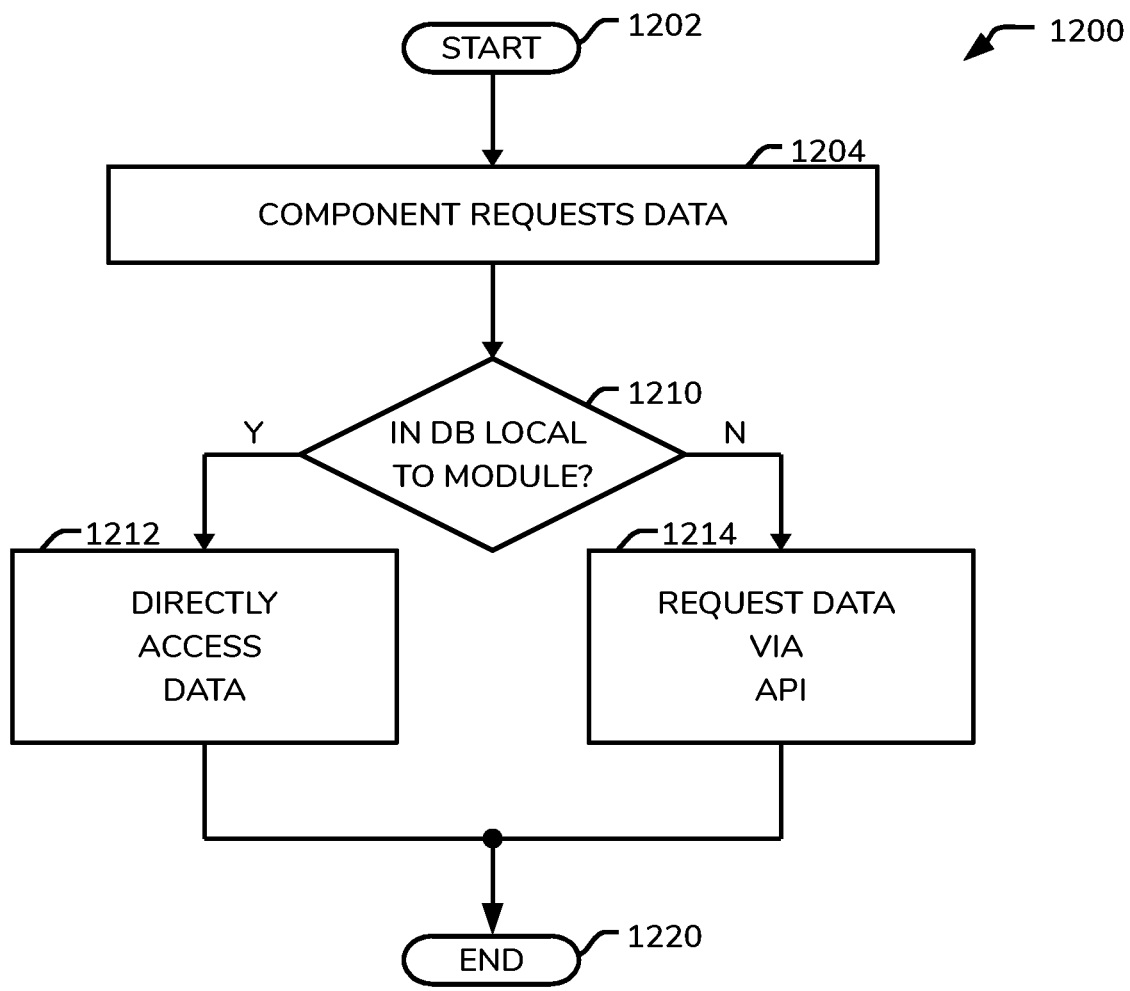
FIG. 12 is a flow chart view of an illustrative data communication operation between siloed databases, according to an embodiment of this disclosure.

Referring now to flowchart 1200 of FIG. 12, an example operation for an illustrative data communication operation between siloed databases will be described, without limitation. Starting with Block 1202, the operation may begin by a component of a requesting entity submitting a request for data (Block 1204).

It may then be determined whether the data requested by the component is stored in an accessible database local to a module, such as a database included by a module with a component making the data request (Block 1210). For the purpose of this example, the locality of the database is relative to being local to a module without regard to being local a computerized device on which the module is operated. If it is determined at Block 1210 that the data is held in accessible database local to the associated module, access to the data may be granted (Block 1212). Alternatively, if it is determined at Block 1210 that the data is not held in a locally accessible database, an API request may be transmitted from the requesting entity to a connected providing entity, such as a communicably connected module and corresponding database (Block 1214). After completion of the operations of Block 1212 or 1214, the operation may then terminate at Block 1220.

Figure 13:
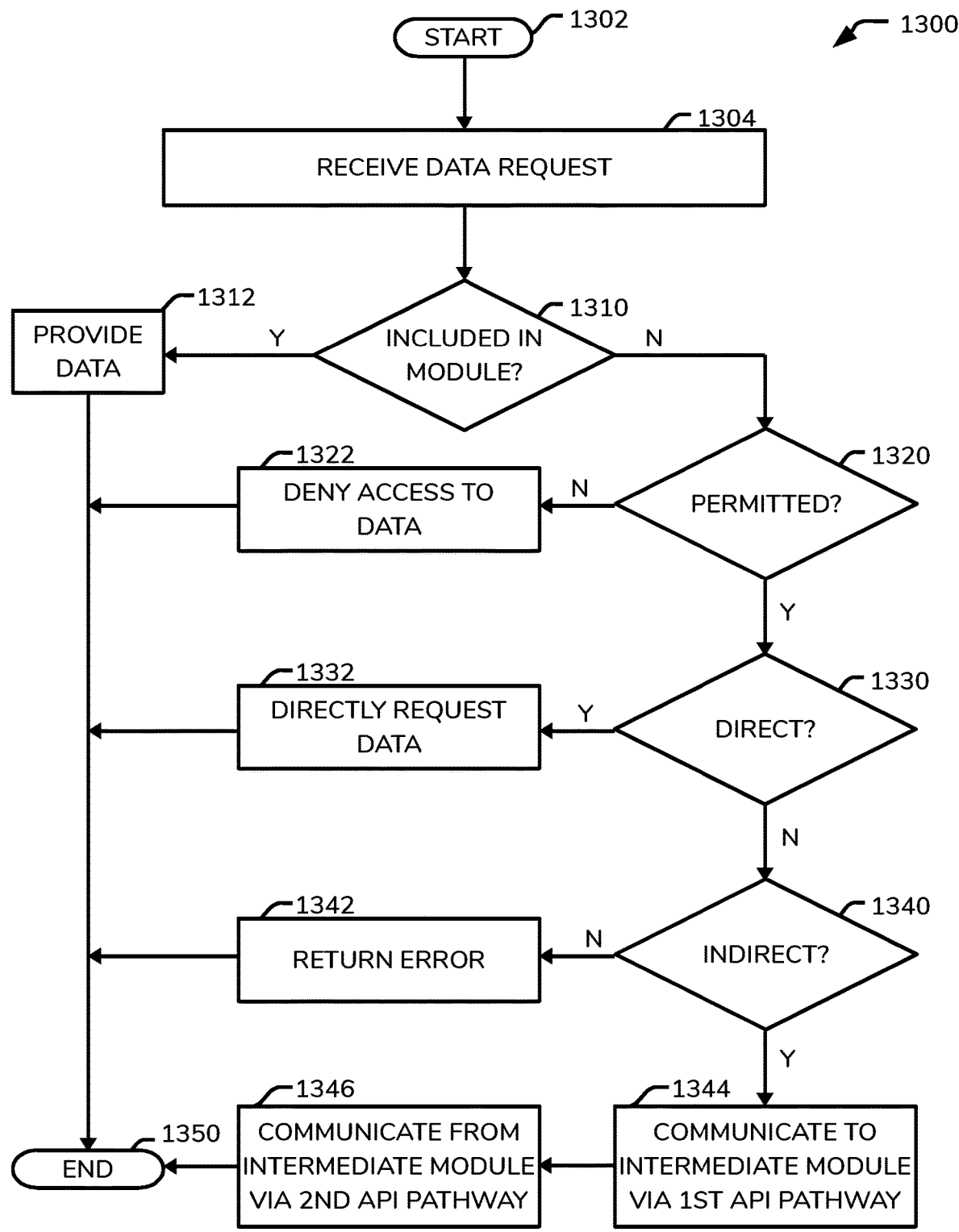
FIG. 13 is a flow chart view of illustrative intra-module and inter-module data communication operations, according to an embodiment of this disclosure.

Referring now to flowchart 1300 of FIG. 13, an example method for illustrative intra-module and inter-module data communication operations will be described, without limitation. Starting with Block 1302, the operation may begin by a providing entity, such as a module, receiving a data request from a requesting party, such as a communicably connected module (Block 1304).

It may then be determined whether the requesting entity making the data request is included by the module including the database from which the data is being requested (Block 1310). If it is determined at Block 1310 that the requesting entity is included in the module, the data may be provided to the requesting entity (Block 1312). The operation may then proceed to Block 1350. Alternatively, if it is determinate Block 1310 that the requesting entity is not included in the module that includes the database from with the request is directed, it may then be determined whether the requesting entity has sufficient permission to access the data from a database associated with another module (Block 1320).

If it is determined at Block 1320 that the requesting entity lacks sufficient permissions to access the data, access to the data may be denied (Block 1322). The operation may then proceed to Block 1350. If it is determinate Block 1320 that the requesting entity has sufficient permission to access the data, it may then be determined whether the requesting entity is directly connected to the module providing the data via a direct API pathway (Block 1330).

If it is determined at Block 1330 that the requesting entity is directly connected to the providing entity via a direct API pathway, the requested data may be communicated via the direct API pathway (Block 1332). The operation may then proceed to Block 1350. If it is determined at Block 1330 that the requesting entity is not directly connected to the providing entity via a direct pathway, it may then be determine whether the requesting entity is indirectly connected to the providing entity via multiple API pathways by way of an intermediary module (Block 1340).

If it is determined at Block 1340 that the requesting entity is not indirectly connected to the providing entity via multiple API pathways, the data communication may be unable to occur and an error may be returned (Block 1342). Alternatively, it if is determined at Block 1340 that the requesting entity is indirectly connected to the providing entity via multiple API pathways, the providing entity may relay the data to the intermediary entity via a first API pathway (Block 1344). The intermediary entity may then relay the data intended for the receiving entity via a second API pathway (Block 1346). Those having skill in the art will appreciate that multiple intermediary entities may be included, which may transmit data intended for a receiving entity via additional API pathways, without limitation. The operation may then terminate a Block 1350.

Figure 14:
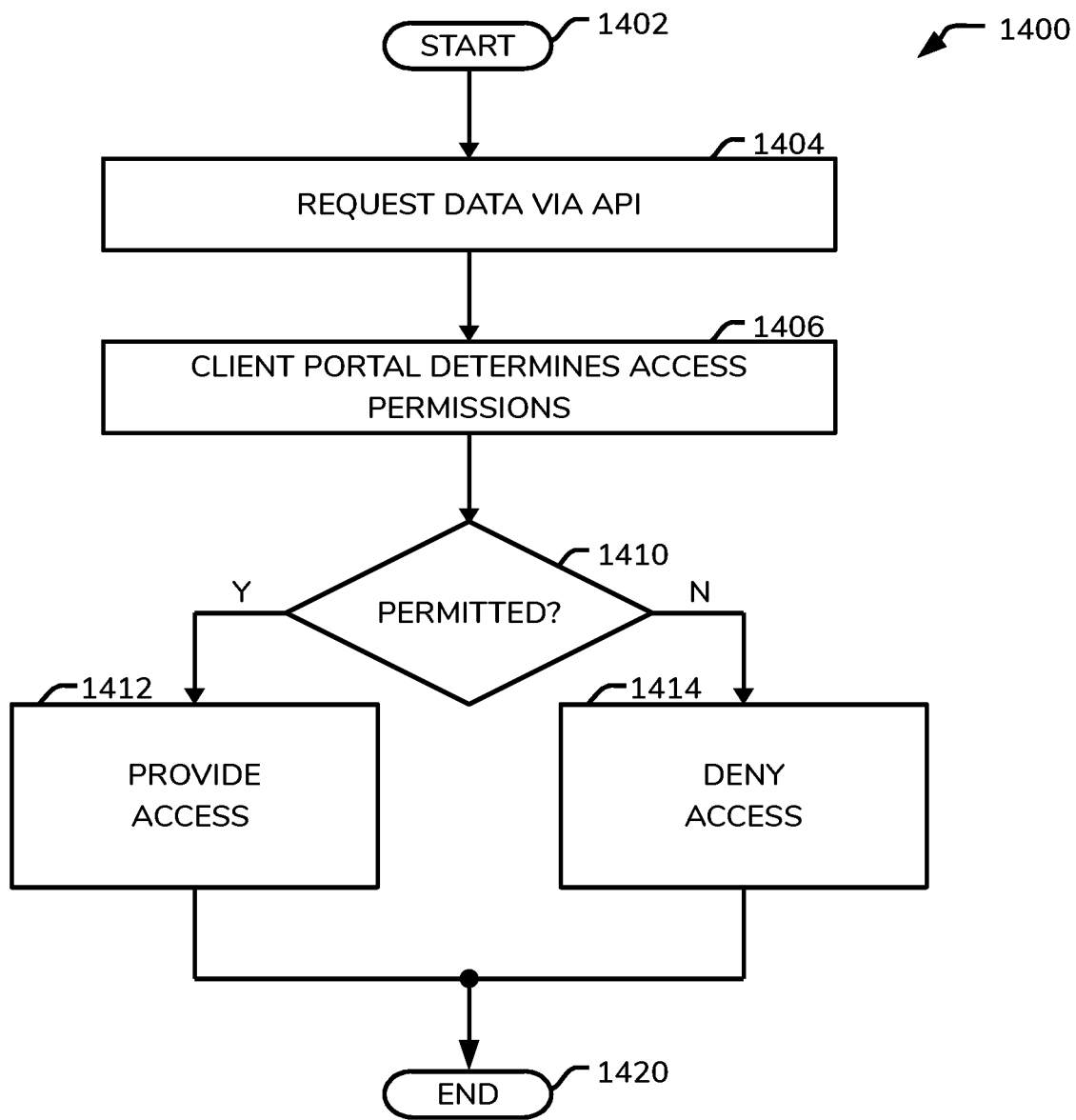
FIG. 14 is a flow chart view of illustrative intra-module and inter-module data permissions operations, according to an embodiment of this disclosure.

Referring now to flowchart 1400 of FIG. 14, an example method for intra-module and inter data permissions operations will be described, without limitation. Starting with Block 1402, data may be requested by a requesting entity via an API (Block 1404). The request may be shared with an entity tasked with managing permissions relating to communication of data between entities, such as the client portal module (Block 1406).

It may then be determined whether the transfer of data between the requesting entity and the providing entity is enabled with sufficient permissions (Block 1410). If it is determined at Block 1410 that sufficient permissions exist for the communication of data from the providing entity to the receiving entity, the data may be communicated (Block 1412). Alternatively, if it is determined at Block 1410 that insufficient permissions exist, the data transmission may be denied (Block 1414). After the operation of Blocks 1412 or 1414, the operation may then terminate at Block 1420.

In one embodiment, the modules provided and described throughout this disclosure may be used in the context of facilitating response to a health crisis, such as may be caused by disease outbreak or viral pandemic. For example, a system enabled by this disclosure may be used to facilitate contact tracing, response and management of an outbreak, and mitigation procedures related to a viral outbreak, such as may be caused by SARS-CoV-2, or another disease, without limitation.

In this example, a system enabled by this disclosure may provide an easy-to-use portal for subscribers to access data relating to their condition and encourage cultural awareness and knowledge regarding personal health and the health of others. For example, the threat assessment assistance module may be leveraged for contact tracing, self-reporting of well-being, reporting of others that appear to have impaired health, access to guest users to provide feedback regarding contact with known infected persons, and other use cases that correlate with the above description. In this example, a known infected user may correlate with a person of concern, and their activity as they interact with society may correlate with worrisome behavior.

In this example, data security and privacy may be maintained such as described above. The various modules discussed throughout this disclosure may continue to be associated with corresponding databases, having access to other information associated with other modules via API requests. Privacy of information may be maintained as discussed above. Subscribers may control permissions to their data, allowing selective access to health responders, governments, employers, family, and others deemed necessary by the subscriber or the customer to have such access.

In this example, location information relating to an infected individual, which may be treated as a person of concern, may be monitored via location tracking. Techniques for location tracking may include GPS, triangulation, cellular radio signals, Wi-Fi signals, Bluetooth, self-reporting, and other techniques for determining the location of an individual that will be apparent to a person of skill in the art after having the benefit of this disclosure. For example, infected individuals may be requested to perform check-ins, which may correlate with wellness checks as discussed above. Additionally, location data may be monitored to correspond with check-ins to facilitate contact tracing and self-isolation.

In this example, educational content may be shared with users, including infected individuals, healthcare professionals, and others involved in the management and/or mitigation of a health crisis or outbreak. Behavioral messaging may be provided to an infected person, which may provide support for mental well-being. Feedback may be requested from the infected individual regarding their perceived mental wellness. At least part of this information may be distributed via the learning portal module discussed above, with access to information being provided consistent with this disclosure. Users may advantageously trust and rely on information provided through the learning portal module, which may be curated or otherwise selected by professionals or others with knowledge in the field of infectious diseases and other health-related topics.

In one embodiment of this example, medical practitioners may import information relating to a patient, which may be associated with the patient profile. This data may be maintained via the client portal module, the threat assessment assistance module, and/or other modules and associated databases, without limitation. In this example, a patient's doctor may select relevant educational content such as videos, written information, and other information the doctor believes is helpful to the patient.

Additionally, patients may provide information for their healthcare professionals, for example, test results, appointments with healthcare professionals, and other information that may affect diagnosis or advice regarding the patient's health. Laboratories may advantageously provide information relating to the patient, such as positive or negative test results indicating whether an infection has occurred. Results from the laboratory may be shared with healthcare professionals, the patient, and other parties as permitted by the parties in charge of managing permissions. Likewise, doctors may share notes, diagnoses, interpretations of lab results, and other information among other professionals.

In this example, additional sources of information may be associated with the profile of a user. For example, biometric devices may provide biometric data relating to a patient or other user. Biometric devices may include heart rate sensors, smart watches, exercise trackers, vitality sensors, and other devices including capabilities for monitoring and detecting biometric conditions of a person. Alerts may be transmitted to a patient or other user upon detection of an anomaly in that patient's physical or mental wellbeing. Such alerts may be communicated via the client portal module, mobile application module, or otherwise.

At least part of the information provided in this example may be analyzed by the machine learning engine discussed above. For example, the machine learning engine may compare various points of data from various sources to determine correlations that may suggest statistical probabilities of an ongoing medical condition or potential impact on society. In some cases, the machine learning engine may be able to anticipate prospective patients at high risk of possible infection. These high-risk patients may be requested to seek testing to confirm whether a viral infection has occurred in that patient. Data determined through operation of the machine learning engine may be anonymized and aggregated in such a way to predict trends, patterns, and other useful information that may assist in the response to an outbreak or pandemic.

In this example, the response coordination module may assist with allocating professionals and resources to respond to an outbreak or other health crisis. For example, upon determining a high prevalence of new infections in a geographic area, it may be indicated that an outbreak is occurring or likely to occur. Responders may be mobilized to address the potential outbreak before such an outbreak gets out of control. Additionally, resources such as ventilators, test, PPE, mask, and other equipment may be allocated for delivery to the location of a detected or potential outbreak.

In this example, additional correlations may be made between the detection of a potential health crisis and other effects on society, such as crime, trauma, violence, and other situations discussed throughout this disclosure. Information may be considered such as whether the prevalence of an outbreak tends to increase the likelihood of worrisome behavior in persons of concern, whether distance to the center of an outbreak or a medical treatment center affects these determinations, if weather or environmental aspects affect the nature of a health crisis and/or worrisome behavior of persons of concern, or other relevant information.

A system enabled by this disclosure, such as a system consistent with this example, may be deployed by governments, schools, workplaces, organizations, households, families, and other groups seeking insight and control over data relating to a health crisis and other traumatic events that may occur in the shadow of the health crisis.

Employers may require employees to participate in such a system as enabled by this disclosure as guest users, such as discussed above, for example in the context of an outreach component. Should an employee become infected with a virus or other condition, the employee may be directed to become a full member of such a system. A schedule may be provided for the employee for self-quarantining, isolation, mental well-being, physical well-being, check-ins, and clearance that the viral infection has subsided. A system enabled by this disclosure may additionally provide an all clear condition for patients or other users that have successfully overcome an infection and are ready to be reintegrated into society.

Gamification features may be provided such as described above to this example, encouraging users to participate in self-reporting, self-quarantining, and other aspects that contribute to mitigating the disastrous effects of an outbreak or pandemic. Feedback may be requested to improve the platform, to better determine professionals and resources for deployment, and to otherwise improve the system.

While various aspects have been described in the above disclosure, the description of this disclosure is intended to illustrate and not limit the scope of the invention. The invention is defined by the scope of the appended claims and not the illustrations and examples provided in the above disclosure. Skilled artisans will appreciate additional aspects of the invention, which may be realized in alternative embodiments, after having the benefit of the above disclosure. Other aspects, advantages, embodiments, and modifications are within the scope of the following claims.

What is claimed is:

1. A threat assessment and response facilitation system operated on a computerized device comprising a processor and memory, the system being operated by execution of electronic instructions stored by and read from the memory, the system comprising:
    modules, wherein a module of the modules comprises:
        a component to execute at least part of the electronic instructions,
        a database siloed with the module and communicably connected to the component to store the at least part of the electronic instructions and data associated with the module, the database being isolated from other modules,
        an application programming interface (API) to communicate with a requesting entity having sufficient permissions at least part of the data included by the database associated with the module and to affect operation of the component included by the module,
        wherein the data stored by the database is directly available to the component of the module, and
        wherein the data stored by the database is selectively available to the requesting entity via the API as governed by the permissions;
    a permissions structure controlled by at least one of the modules designated to manage the permissions to selectively grant access to exchange the at least part of the data stored by the database of the module and request execution of the at least part of the electronic instructions of the component of the module;
    a communication structure controlled by at least one of the modules designated to manage communications to selectively transfer the at least part of the data between the module and the requesting entity as permitted by the permissions structure via the API of the module;
    wherein the electronic instructions, the data, the communications, and/or the permissions are communicated between a discrete API pathway between a first API of a first module and a second API of a second module, each of which being included within the modules and managed by the permissions structure;
    wherein the modules comprise:
        a threat assessment assistance module comprising:
            a profiles and peoples component for identifying a person of concern and organizing the data relating to the person of concern,
            a worrisome behavior component for monitoring worrisome behavior associated with the person of concern,
            an analytics component to analyze information relating to the person of concern to maintain a record and recommend activity corresponding with the record,
            a risk enhancers component for monitoring conditions affecting risk of harm to the person of concern and others,
            a machine learning engine to compare at least part of the data included by the database of the threat assessment assistance module to identify correlations and predict a statistical probability of the worrisome behavior, and
            wherein the machine learning engine is at least partially self-trained in a semi-supervised manner to identify links, correlations, associations, and data patterns indicative of a probability of an outcome given a parameter and/or variable;
        a response coordination module comprising:
            a scheduling component for organizing responders for deployment to a site of a traumatic event,
            a resources component for requesting resources to support the responders, and
            an information management component for caching and managing the information sharable among the responders; and
        a client portal module to provide a user with a graphical interface to view information from the modules communicably connected to the client portal module via the API, the client portal module being operatively connected to an input device operable by the user that, upon the user manipulating the input device, controls operation of at least one connected module of the modules via communication of instructions via the API pathway between the client portal module and the connected module, the client portal module comprising:
            a profiles component for managing the information associated with a user,
            a graphical user interface (GUI) displayable to the user; and
        wherein external applications having the permissions that are sufficient are selectively communicable with at least some of the modules and the data associated with the at least some of the modules for which the access is permitted.

2. The system of claim 1, wherein the threat assessment assistance module further comprises:
    a genogram component to organize the information relating to familial organization including genealogy and the worrisome behavior associated with a family member of the person of concern;
    wherein the information provided by the genogram component is analyzed by the threat assessment assistance module to derive insight relating to the person of concern.

3. The system of claim 1, wherein the threat assessment assistance module further comprises:
    a social media analysis request component to communicate with a third-party data reporting service that monitors social media network activity of the person of concern; and
    wherein the third-party data reporting service communicates with the social media analysis request component via the API.

4. The system of claim 1, wherein the threat assessment assistance module further comprises:
a domains and beliefs component to assess a change in domain-focused factors and a change in belief-focused factors indicative of a change in behavior of the person of concern.

5. The system of claim 1, wherein the threat assessment assistance module is communicably connected to an external web application comprising:
an outreach component to provide a channel of communication for submission of the information relating to the person of concern by a third party, the information being includable in the database of the threat assessment assistance module; and
a self-assessment component to facilitate self-assessment of an emotional condition by the user to be associated with the user.

6. The system of claim 1, wherein the modules further comprise:
a mobile application module to provide access to the client portal module via a portable electronic device and notifications and alerts relating to the user.

7. The system of claim 1, wherein the response coordination module further comprises:
a stipend management component to manage disbursement of stipends and payments relating to the deployment.

8. The system of claim 1, wherein the client portal module further comprises:
a gamification component to reward engagement with the system and provide incentives to continue the engagement.

9. The systems of claim 1, wherein the modules further comprise:
a learning portal module comprising:
educational content stored in the database associated with the learning portal module,
a certificate and accreditation component to manage qualifications for participating in the deployment and access to the at least part of the data associated with the threat assessment assistance module, and
a participation component to manage enrollment, attendance, and grading relating to the educational content.

10. The system of claim 9, wherein the modules further comprise:
a training broker module comprising:
a training seats component to manage an assignment of user rights to participate in events and access the educational content hosted by the learning portal module,
an approvals component to manage the assignment of user rights by a host of the events and the educational content, and
an e-commerce component for managing a transfer of funds associated with the assignment of user rights.

11. The system of claim 1, wherein the modules further comprise a messaging module to provide communication among the users of the modules.

12. The system of claim 1:
wherein the communication structure provides a direct communication pathway between the modules that are directly connected via the API;
wherein the communication structure provides a bridged communication pathway between the modules that are indirectly connected via the API by sharing at least one intermediary module being communicably connected to the modules via the API; and
wherein the intermediary module relays the communication received by a first connected module via a first API pathway to a second connected module via a second API pathway.

13. A threat assessment and response facilitation system operated on a computerized device comprising a processor and memory, the system being operated by execution of electronic instructions stored by and read from the memory, the system comprising:
modules, wherein a module of the modules comprises:
a component to execute at least part of the electronic instructions,
a database with the module and communicably connected to the component to store the at least part of the electronic instructions and data associated with the module,
an application programming interface (API) to communicate with a requesting entity having sufficient permissions at least part of the data included by the database associated with the module and to affect operation of the component included by the module,
wherein the data stored by the database is directly available to the component of the module, and
wherein the data stored by the database is selectively available to the requesting entity via the API as governed by the permissions;
a permissions structure controlled by at least one of the modules designated to manage the permissions to selectively grant access to exchange the at least part of the data stored by the database of the module and request execution of the at least part of the electronic instructions of the component of the module;
a communication structure controlled by at least one of the modules designated to manage communications to selectively transfer the at least part of the data between the module and the requesting entity as permitted by the permissions structure via the API of the module;
wherein the modules comprise:
a threat assessment assistance module comprising:
a profiles and peoples component for identifying an observed person comprising a person of concern, witness, and/or victim and organizing the data relating to the observed person,
a worrisome behavior component for monitoring worrisome behavior associated with the observed person,
an analytics component to analyze information relating to the observed person to maintain a record and recommend activity corresponding with the record,
a machine learning engine to compare the at least part of the data included by the database of the threat assessment assistance module to identify correlations and predict a statistical probability of the worrisome behavior, the machine learning engine being at least partially self-trained in a semi-supervised manner to identify links, correlations, associations, and data patterns indicative of a probability of an outcome given a parameter and/or variable, and
a digital workspace component to facilitate collaboration;
a response coordination module comprising:
a scheduling component for organizing responders for deployment to a site of a traumatic event, a resources component for requesting resources to support the responders, and
an information management component for caching and managing information sharing among the responders; and
a client portal module comprising:
a profiles component for managing the information associated with a user,
a gamification component to reward engagement with the system and incentivize continued engagement;
a messaging module to provide communication among the users of the modules;
wherein external applications having the permissions that are sufficient are selectively communicable with at least some of the modules and the data associated with the at least some of the modules for which the access is permitted;
wherein the communication structure provides a direct communication pathway between the modules that are directly connected via the API;
wherein the communication structure provides a bridged communication pathway between the modules that are indirectly connected via the API by sharing at least one intermediary module being communicably connected to the modules via the API; and
wherein the intermediary module relays the communication received by a first connected module via a first API pathway to a second connected module via a second API pathway.

14. The system of claim 13, wherein the threat assessment assistance module further comprises:
a genogram component to organize the information relating to familial organization including genealogy and the worrisome behavior associated with a family member of the person of concern;
wherein the information provided by the genogram component is analyzed by the threat assessment assistance module to derive insight relating to the person of concern;
a domains and beliefs component to assess a change in domain-focused factors and a change in belief-focused factors indicative of a change in behavior of the person of concern; and
a risk enhancers component for monitoring conditions affecting risk of harm to the person of concern and others.

15. The system of claim 13, wherein the threat assessment assistance module further comprises:
a social media analysis request component to communicate with a third-party data reporting service that monitors social media network activity of the person of concern;
wherein the third-party data reporting service communicates with the social media analysis request component via the API; and
wherein the threat assessment assistance module is communicably connected to an external web application comprising:
an outreach component to provide a channel of communication for submission of the information relating to the person of concern by a third party, the information being includable in the database of the threat assessment assistance module, and
a self-assessment component to facilitate self-assessment of an emotional condition by the user to be associated with the user.

16. The systems of claim 13, wherein the modules further comprise:
a learning portal module comprising:
educational content stored in the database associated with the learning portal module,
a certificate and accreditation component to manage qualifications for participating in the deployment and access to the at least part of the data associated with the threat assessment assistance module, and
a participation component to manage enrollment, attendance, and grading relating to the educational content; and
a training broker module comprising:
a training seats component to manage an assignment of user rights to participate in events and access the educational content hosted by the learning portal module,
an approvals component to manage the assignment of user rights by a host of the events and the educational content, and
an e-commerce component for managing a transfer of funds associated with the assignment of user rights.

17. A method for assessing a threat and facilitating a response using a threat assessment and response facilitation system operated on a computerized device comprising a processor and memory, the system being operated by execution of electronic instructions stored by and read from the memory, the method comprising:
a) operating modules, wherein a module of the modules comprises:
a component to execute at least part of the electronic instructions,
a database siloed with the module and communicably connected to the component to store the at least part of the electronic instructions and data associated with the module,
an application programming interface (API) to communicate with a requesting entity having sufficient permissions at least part of the data included by the database associated with the module and to affect operation of the component included by the module,
wherein the data stored by the database is directly available to the component of the module, and
wherein the data stored by the database is selectively available to the requesting entity via the API as governed by the permissions;
b) managing permissions via a permissions structure to selectively grant access to exchange the at least part of the data stored by the database of the module and request execution of the at least part of the electronic instructions of the component of the module;
c) managing communications via a communication structure to selectively transfer the at least part of the data between the module and the requesting entity as permitted by the permissions structure via the API of the module;
d) providing a direct communication pathway between the modules that are directly connected via the API;
e) providing a bridged communication pathway between the modules that are indirectly connected via the API by sharing at least one intermediary module being communicably connected to the modules via the API, wherein the intermediary module relays the communication received by a first connected module via a first API pathway to a second connected module via a second API pathway;
wherein the modules comprise:

a threat assessment assistance module for:
- i) identifying a person of concern and organizing the data relating to the person of concern via a profiles and peoples component,
- ii) monitoring worrisome behavior associated with the person of concern via a worrisome behavior component,
- iii) analyzing information relating to the person of concern to maintain a record and recommend activity corresponding with the record via an analytics component, and
- iv) monitoring conditions affecting risk of harm to the person of concern and others via a risk enhancers component;

a response coordination module for:
- v) organizing responders for deployment to a site of a traumatic event via a scheduling component,
- vi) requesting resources to support the responders via a resources component, and
- vii) caching and managing information sharing among the responders via an information management component; and a client portal module for:
- viii) managing the information associated with a user via a profiles component,
- ix) displaying a graphical user interface (GUI) to the user; and f) comparing at least part of the data included by the database of the threat assessment assistance module to identify correlations and predict a statistical probability of the worrisome behavior via a machine learning engine, the machine learning engine being at least partially self-trained in a semi-supervised manner to identify links, correlations, associations, and data patterns indicative of a probability of an outcome given a parameter and/or variable;

g) selectively communicating among external applications having the permissions that are sufficient and at least some of the modules and the data associated with the at least some of the modules for which the access is permitted; and h) providing the communications among the users of the modules via a messaging module.

18. The method of claim 17, wherein operating the threat assessment assistance module further comprises the steps:
- x) organizing the information relating to familial organization including genealogy and the worrisome behavior associated with a family member of the person of concern via a genogram component;
- xi) analyzing the information provided by the genogram component by the threat assessment assistance module and deriving insight relating to the person of concern from the information;
- xii) communicating with a third-party data reporting service that monitors social media network activity of the person of concern via a social media analysis request component, wherein the third-party data reporting service communicates with the social media analysis request component via the API; and
- xiii) predicting a change in behavior of the person of concern via a domains and beliefs component by assessing a change in domain-focused factors and a change in belief-focused factors.

19. The method of claim 17, wherein the modules further comprise:

a learning portal module for:
- xiv) distributing educational content stored in the database associated with the learning portal module,
- xv) managing qualifications for participating in the deployment and the access to the at least part of the data associated with the threat assessment assistance module via a certificate and accreditation component, and
- xvi) managing enrollment, attendance, and grading relating to the educational content via a participation component.

* * * * *